United States Patent
Cao et al.

(10) Patent No.: US 11,802,311 B2
(45) Date of Patent: Oct. 31, 2023

(54) METHODS OF QUANTIFYING RNA AND DNA VARIANTS THROUGH SEQUENCING EMPLOYING PHOSPHOROTHIOATES

(71) Applicant: Massachusetts Institute of Technology, Cambridge, MA (US)

(72) Inventors: Bo Cao, Cambridge, MA (US); Peter C. Dedon, Boston, MA (US); Jennifer F. Hu, Cambridge, MA (US); Michael S. DeMott, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 963 days.

(21) Appl. No.: 16/248,729

(22) Filed: Jan. 15, 2019

(65) Prior Publication Data

US 2019/0284624 A1  Sep. 19, 2019

Related U.S. Application Data

(60) Provisional application No. 62/643,426, filed on Mar. 15, 2018.

(51) Int. Cl.
  *C12Q 1/6874* (2018.01)
  *C12N 15/10* (2006.01)
  *C12Q 1/6869* (2018.01)

(52) U.S. Cl.
  CPC ....... *C12Q 1/6874* (2013.01); *C12N 15/1096* (2013.01); *C12Q 1/6869* (2013.01)

(58) Field of Classification Search
  CPC . C12Q 1/6874; C12Q 1/6869; C12N 15/1096
  See application file for complete search history.

(56) References Cited

U.S. PATENT DOCUMENTS

| | | | |
|---|---|---|---|
| 7,270,958 B2 * | 9/2007 | Makarov | C12Q 1/6855 435/6.1 |
| 2013/0225421 A1 | 8/2013 | Chen et al. | |
| 2017/0321210 A1 * | 11/2017 | Nishida | C12Y 302/02027 |
| 2018/0355406 A1 * | 12/2018 | Glover | C12Q 1/6886 |

FOREIGN PATENT DOCUMENTS

| | | |
|---|---|---|
| CN | 104630211 B | 3/2018 |
| WO | WO 2004/024749 A2 | 3/2004 |
| WO | WO 2017/032808 A1 | 3/2017 |

OTHER PUBLICATIONS

Sood et al. ("DNAmod: the DNA modification database." (2016) 1-13). (Year: 2016).*
Extended European Search Report for EP 19767632.3 dated Feb. 11, 2022.

(Continued)

*Primary Examiner* — Jeremy C Flinders
(74) *Attorney, Agent, or Firm* — Wolf, Greenfield & Sacks, P.C.

(57) ABSTRACT

This disclosure provides methods and compositions for analyzing nucleic acids such as DNA and RNA, and including determination of absolute numbers of such nucleic acids and/or detection and localization of lesions or other modifications on such nucleic acids.

22 Claims, 14 Drawing Sheets

Specification includes a Sequence Listing.

(56) References Cited

OTHER PUBLICATIONS

Silas et al., A Small RNA Isolation and Sequencing Protocol and Its Application to Assay CRISPR RNA Biogenesis in Bacteria. Bio Protoc. Feb. 20, 2018;8(4):e2727. doi: 10.21769/BioProtoc.2727. PMID: 29600253; PMCID: PMC5870890.

Xu et al., An improved protocol for small RNA library construction using High Definition adapters. Methods Next Gen Seq. Jan. 1, 2015;2(1):1-10.

International Search Report and Written Opinion for PCT/US2019/013714, dated May 8, 2019.

International Preliminary Report on Patentability for PCT/US2019/013714, dated Sep. 24, 2020.

Cao et al., Genomic mapping of phosphorothioates reveals partial modification of short consensus sequences. Nat Commun. Jun. 5, 2014;5:3951. doi: 10.1038/ncomms4951.

Cai et al., A Platform for Discovery and Quantification of Modified Ribonucleosides in RNA: Application to Stress-Induced Reprogramming of tRNA Modifications. Methods Enzymol. 2015;560:29-71. PMCID: PMC4774897.

Chiu et al., GBshape: a genome browser database for DNA shape annotations. Nucleic Acids Research. 2014.

Gu et al., tRNA modifications regulate translation during cellular stress. FEBS Lett. 2014;588(23):4287-96. PMCID: 4403629.

Hafner et al., RNA-ligase-dependent biases in miRNA representation in deep-sequenced small RNA cDNA libraries. RNA. 2011;17(9):1697-712. PMCID: PMC3162335.

Li et al., Human genome-wide repair map of DNA damage caused by the cigarette smoke carcinogen benzo [a]pyrene. Proc Natl Acad Sci U S A. 2017;114(26):6752-7. PMCID: PMC5495276.

Linsen et al., Limitations and possibilities of small RNA digital gene expression profiling. Nat Methods. 2009;6(7):474-6.

Pang et al., Diverse cell stresses induce unique patterns of tRNA up- and down-regulation: tRNA-seq for quantifying changes in tRNA copy number Nucleic Acids Res. 2014;42(22):e170. PMCID: 4267671.

Phizicky et al., tRNA biology charges to the front. Genes Dev. 2010;24(17):1832-60. PMCID: 2932967.

Tate et al., Evaluation of circular DNA substrates for whole genome amplification prior to forensic analysis. Forensic Sci Int Genet. 2012;6(2):185-90.

Zhang et al., High-efficiency RNA cloning enables accurate quantification of miRNA expression by deep sequencing. Genome Biol. 2013;14(10):R109. PMCID: PMC3983620.

Zheng et al., Efficient and quantitative high-throughput tRNA sequencing. Nature Methods. 2015;12:835-7.

Zhou et al., Mapping genomic hotspots of DNA damage by a single-strand-DNA-compatible and strand-specific ChIP-seq method. Genome Res. 2013;23(4):705-15. PMCID: PMC3613587.

\* cited by examiner

5'-G$_{PT}$T$_{PT}$T$_{PT}$C$_{PT}$C$_{PT}$T$_{PT}$T$_{PT}$T$_{PT}$GGTGCCCGAGTG-OH-3'

PT: phosphothioate linkage

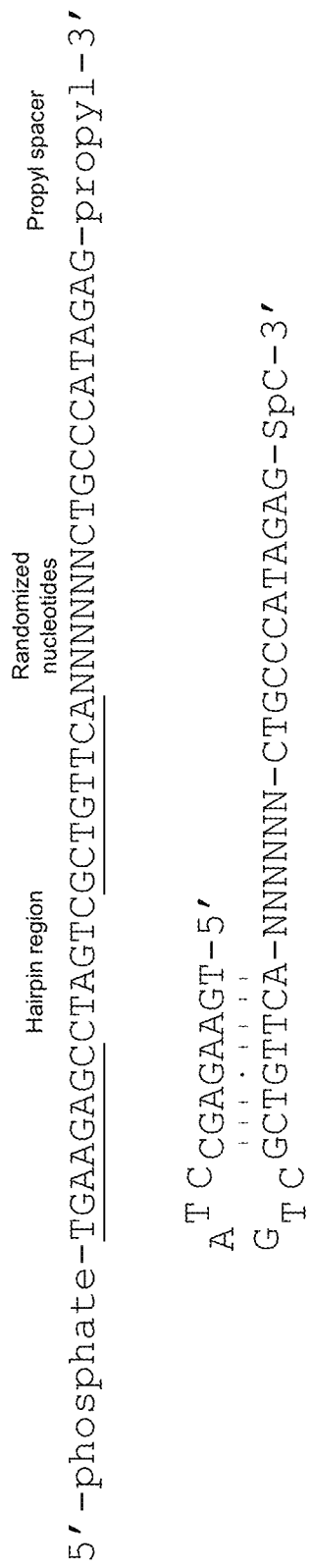
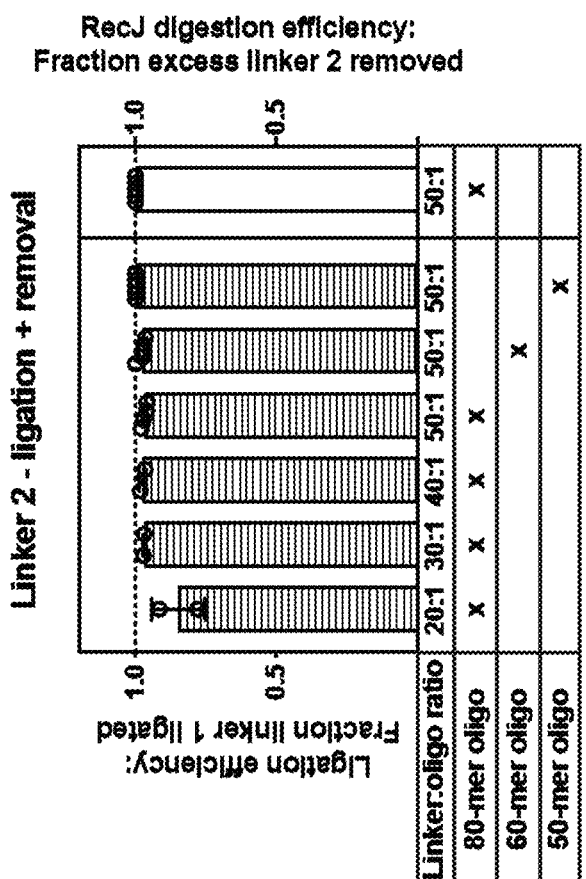
Figure 5

Illumina PCR primer 1

5'-AATGATACGGCGACCACCGAGATCTACACXXXXXXXXACACTCTTTCCCTACACGACGCTCTTCCGATCTCTTGAACAGGCGACTAGGCTCTTCA-3'

Illumina i5 anchor     Sample-identifying barcode sequence                                          Reverse complementary to 5' end of Linker 2

Illumina PCR primer 2

5'-CAAGCAGAAGACGGCATACGAGATXXXXXXXXCGGTCTCGGCATTCCTGCTGAACCGCTCTTCCGATCTGTCTTGGTGCCCGAGTG-3'

Illumina i7 anchor     Sample-identifying barcode sequence                                            Reverse complementary to 3' end of Linker 1

Figure 6

METHODS OF QUANTIFYING RNA AND DNA VARIANTS THROUGH SEQUENCING EMPLOYING PHOSPHOROTHIOATES

RELATED APPLICATIONS

This application claims the benefit under 35 U.S.C. § 119(e) of U.S. Provisional Application No. 62/643,426, filed Mar. 15, 2018, the entire contents of which are incorporated by reference herein.

FEDERALLY SPONSORED RESEARCH

This invention was made with Government support under Grant Nos. UFDSP00010445, CHE-1709364 and CHE-1019990 awarded by the National Science Foundation, and Grant No. 1R01ES024615 awarded by the National Institutes of Health. The Government has certain rights in the invention.

BACKGROUND

Modern biological and biomedical research has been transformed by the so-called "'omic" technologies, in which analytical technologies capture information about thousands and even millions of biomolecules in a single experiment, as opposed to older technologies capable of analyzing only one or a few molecules at a time. Included in the realm of omics is the idea of analyzing the expression of genes on a genome-wide scale rather than one gene at a time. For example, one aspect of functional genomics focuses on the dynamics of gene transcription in a specific context. The advent of next generation sequencing (NGS) technology has enabled massively parallel quantification of all RNA transcripts present in a cell at a given moment.

DNA sequencing technology also allows us to determine the linear sequence of all 3 billion nucleotides in the human genome, which has revealed the existence of ~20,000 genes that code for proteins comprised in cells, tissues and organs. Whole genome sequencing provides critical information about genetic variation among individuals and disease-causing mutations. Examples include mutations that arise in DNA in cells subjected to numerous chemical insults that damage the sugar-phosphate backbone. This produces breaks in the DNA strands, as well as the nucleobases. Cells have evolved elaborate DNA repair systems to detect and repair DNA damage. Chemical modification of DNA also serves as a means to control gene expression in eukaryotes, to fend off viral invaders in prokaryotes as part of restriction-modification systems, or to shield a viral genome from attack by restriction-modification enzymes. Among these chemical modifications, the addition of methyl groups to 2'-deoxycyditine nucleotides (m5C) in DNA has emerged as an important mechanism in controlling gene expression in human cells. DNA sequencing technology has proved useful in defining the locations of certain specific modifications.

However current methodologies have their limitations, as discussed in greater detail herein. This disclosure provides methods that address and overcome such limitations.

SUMMARY

This disclosure therefore provides methods and products for detecting, quantitating and sequencing nucleic acids, especially RNAs. This disclosure further provides methods and kits for detecting nucleic acid modifications such as but not limited to methylation events. These are discussed in greater detail below.

Various methods of the present disclosure enable a direct, linear correlation between the sequencing read counts and the number of copies of all RNA molecules within the same sample. Unlike other RNA sequencing methods, which allow only relative quantification of changes in the levels of RNA molecules between different samples, the method described here enables absolute quantification of different RNA molecules in the same sample, which allows quantitative definition of landscape of RNA molecules in a cell or tissue at any given moment. This process can be applied to RNA from any source, with multiplexing to accommodate many samples, and it can be used to investigate gene expression, RNA metabolism, RNA stability, RNA therapeutics, and other problems related to quantitative analysis of RNA molecules. The method has been reduced to practice in an application demonstrating changes in the levels of RNA molecules less than 200 nucleotides in length, including microRNA molecules, transfer RNA (tRNA) molecules, and RNA fragments from tRNA and other types of noncoding RNA. The resulting profile of all small RNA molecules in a cell reveals previously unobserved features of the RNA landscape and novel behaviors of specific RNA molecules, such as differences in the levels of the dozens of tRNA isoacceptors in a cell. The method will find wide application in many fields of biological and biomedical research and development in academia and in the clinic.

The present disclosure provides a means to quantitatively measure the number of copies of each different type and sequence of RNA molecule in a single sample. The method will be useful in the disciplines of functional genomics, molecular and cell biology, microbiology and other biomedical and biological areas. The breadth of applicability of the method stems from the need to know, in many instances, how many copies of each type of RNA exist in a cell or tissue sample at any given moment.

Thus, this disclosure provides the following aspects and embodiments:

One aspect provides a method for measuring RNA in a sample comprising (a) dephosphorylating RNA in a sample, optionally using alkaline phosphatase, thereby generating dephosphorylated RNA, (b) ligating, to the dephosphorylated RNA, a ddNTP-ended oligodeoxynucleotide linker having two or more randomized nucleotides at its 5'-end (Linker 1), thereby generating a linker-ligated RNA, optionally wherein the ddNTP-ended oligodeoxynucleotide linker is dideoxycytidine-ended oligodeoxynucleotide linker, (c) treating the linker-ligated RNA conjugate with an AlkB enzyme capable of reducing level of RNA modification, optionally wherein the AlkB enzyme is a mutant AlkB enzyme or wherein the AlkB enzyme comprises a mixture of wild type and mutant variants with slightly differing demethylation targets, (d) removing excess Linker 1 by treating with deadenylase to remove a ligase-mediated intermediate and then degrading Linker 1 with the 2'-deoxyribonuclease Rec J, (e) reverse transcribing the linker-ligated RNA into cDNA using a primer complementary to Linker 1 and reverse transcriptase, optionally wherein the reverse transcriptase comprises a mixture of enzymes with slightly differing fidelities and susceptibilities to modifications, (f) degrading residual RNA, including optionally RNA that is not linker-ligated, optionally using alkaline hydrolysis, (g) ligating a hairpin/splint oligodeoxynucleotide linker (Linker 2) to the cDNA, optionally using T4 DNA ligase, thereby generating a linker-ligated cDNA, (h) removing excess Linker 2 by treating with deadenylase to remove a ligase-mediated intermediate and then degrading Linker 2 with the 2'-deoxyribonuclease Rec J, and (i) sequencing the linker-ligated cDNA using Primer 1 and Primer 2, optionally wherein Primers 1 and 2 partially comprise or consist of the reverse complements of sequences in Linkers 1 and 2 in the linker-ligated cDNA.

In some embodiments, the RNA are purified RNA.

In some embodiments, the RNA are less than or about 200 nucleotides in length, or less than or about 100 nucleotides in length, including 2-200 nucleotides in length or 2-100 nucleotides in length or 15-200 nucleotides in length or 15-100 nucleotides in length.

In some embodiments, the RNA are between about 200 to about 1000 nucleotides in length, or between about 200 to about 5000 nucleotides in length.

In some embodiments, the RNA are or comprise tRNA or miRNA.

In some embodiments, ligating of step (b) is performed in the presence of a T4 RNA ligase. In some embodiments, the ligating of step (b) results in >91% or >95% ligation efficiency.

In some embodiments, the method measures the number of a plurality of different RNA molecules in a sample. In some embodiments, the method measures absolute quantity of a plurality of different RNA in a sample. In some embodiments, the plurality is at 2-10, 2-20, 2-30, 2-40, 2-50, 2-60, 2-70, 2-80, 2-90, or 2-100, or more.

In some embodiments, the RNA is present in a sample, wherein the sample is prepared from and/or contains cells or tissue.

In some embodiments, the ddNTP-ended oligodeoxynucleotide linker has two randomized nucleotides at its 5'-end. In some embodiments, the ddNTP-ended oligodeoxynucleotide linker is a dideoxycytidine-ended oligodeoxynucleotide linker.

In some embodiments, the hairpin/splint oligodeoxynucleotide linker comprises a double-stranded stem region, a single-stranded loop region, a random nucleotide sequence region capable of hybridizing to the cDNA, and a single-stranded 3' end.

In some embodiments, the method generates a library of linker-ligated cDNA representative of starting RNA.

In some embodiments, Linker 1 has a nucleotide sequence of 5'-phosphate-NN-CACTCGGGCACCAAGGA-ddC-3' (SEQ ID NO: 1). In some embodiments, Linker 1 has a nucleotide sequence of 5'-phosphate-NN-CACTCGGGCACCAGGA-ddC-3' (SEQ ID NO: 2). In some embodiments, the primer complementary to Linker 1 (RT primer) is a oligodeoxynucleotide primer comprising one or more phosphorothioate linkages at the 5'-end. In some embodiments, the primer complementary to Linker 1 comprises 2, 3, 4, 5, 6, 7, 8, 9, 10, or more phosphorothioate linkages at the 5'-end. In some embodiments, the primer complementary to Linker 1 is a oligodeoxynucleotide primer possessing 6 phosphorothioate linkages at the 5'-end.

In some embodiments, the primer complementary to Linker 1 has a sequence of 5'-$G_{PT}T_{PT}C_{PT}C_{PT}T_{PT}T_{PT}$GGTGCCCGAGTG-OH-3', wherein PT represents phosphorothioate (SEQ ID NO: 3).

In some embodiments, the residual RNA is degraded by incubation with sodium hydroxide.

In some embodiments, the hairpin/splint oligodeoxynucleotide linker comprises a random nucleotide sequence region that is 4, 5, 6, 7, 8, 9, 10 or more nucleotides in length, wherein the nucleotides are randomized nucleotides, optionally wherein the random nucleotide sequence region is 6 nucleotides in length, optionally wherein the random nucleotide sequence is complementary to the 3' end of the cDNA.

In some embodiments, the hairpin/splint oligodeoxynucleotide linker comprises a sequence as shown in FIG. 5.

In some embodiments, the hairpin/splint oligodeoxynucleotide linker comprises a 3'-propyl group capable of preventing self-ligation, at its 3' end.

In some embodiments, Primer 1 has a nucleotide sequence as shown in FIG. 6. In some embodiments, Primer 2 has a nucleotide sequence as shown in FIG. 6.

In some embodiments, Primer 1 is a reverse complement of the 5' end of Linker 2, optionally wherein Primer 1 is a reverse complement of the 5' end of Linker 2 that is 5-50, 10-50, 20-50, or about 20, 21, 22, 23, 24 or 25 nucleotides in length, further optionally wherein it is 22 nucleotides in length.

In some embodiments, Primer 2 is a reverse complement of the 5' end of Linker 1, optionally wherein Primer 2 is a reverse complement of the 5' end of Linker 1 that is 5-50, 10-50, 15-50, or about 15, 16, 17, 18, 19 or 20 nucleotides in length, further optionally wherein it is 18 nucleotides in length.

Another aspect provides a kit comprising DNA oligonucleotides, optionally Linkers 1 and 2, and further optionally Primers 1 and 2, an RNA and a DNA ligase, optionally T4 RNA ligase and T4 DNA ligase, and a buffer.

In some embodiments, the kit further comprises a high processivity, high accuracy, thermostable reverse transcriptase. The reverse transcriptase may be a mixture of enzymes with slightly differing fidelities and susceptibilities to modifications.

In some embodiments, the kit further comprises alkaline phosphatase.

In some embodiments, the kit further comprises AlkB enzyme, optionally wherein AlkB enzyme is a mutant AlkB enzyme or wherein it comprises a mixture of wild type and mutant variants with slightly differing demethylation targets.

In some embodiments, the kit further comprises an RNase inhibitor.

In some embodiments, the kit further comprises deadenylase, optionally 5'-deadenylase.

In some embodiments, the kit further comprises Rec J enzyme.

In some embodiments, the kit further comprises an RNA purification kit and/or reagents.

In some embodiments, the kit further comprises sodium hydroxide and/or hydrochloric acid.

In some embodiments, the kit further comprises PEG, optionally PEG8000.

In some embodiments, one or more, including all, components are housed in separate containers.

Various methods of this disclosure also address the significant unmet need for a widely applicable DNA sequencing method to map a variety of DNA features, including for example across genomes in DNA isolated from cells, tissues, or other sources such as fecal DNA for analyzing the gut microbiome.

The present disclosure therefore also provides a quantitative means to localize DNA features in entire genomes at single-nucleotide resolution. The method, Nick-seq™, is useful in the disciplines of genetics, genomics, molecular and cell biology, microbiology, biotechnology, medicine, toxicology, pharmacology and other biomedical and biological areas. The breadth of applicability of the method results from the need for genomic maps of DNA features in all of these disciplines for biomedical research and development in academia, government and industry.

The methods provided herein enable one skilled in the art to selectively label DNA at sites of strand-breaks, to use this labeled DNA for deep-sequencing analysis, and to then localize the sites of strand-breaks within a genome or to identify the biological source of the labeled DNA based on its sequence. This disclosure combines the ability to (1) selectively label sites of DNA strand-breaks with nuclease-resistant nucleotides and (2) degrade the unlabeled DNA with a nuclease that will not degrade the labeled DNA, which allows deep-sequencing of the labeled DNA for subsequent localization of the strand-break in the genome. The site of the original DNA nicks will be evident as the 5'-most nucleotide of the sequenced DNA fragments.

Thus, this disclosure provides the following aspects and embodiments:

One aspect provides a method for analyzing nucleic acids comprising
(a) incubating a nucleic acid with a polymerase and a ddNTP under conditions sufficient to fill in one or more single-stranded nicks in the nucleic acid,
(b) treating the nucleic acid to convert a nucleic acid modification into a single-stranded nick, thereby generating a nicked nucleic acid,
(c) incubating the nicked nucleic acid with a polymerase and alpha-thio-dNTPs under conditions sufficient to generate a phosphorothioate-labeled nucleic acid fragment,
(d) optionally removing unlabeled nucleic acids under conditions that specifically degrade said unlabeled nucleic acids and do not degrade the phosphorothioate-labeled nucleic acid fragment, and/or
(e) optionally isolating or purifying the phosphorothioate-labeled nucleic acid fragment, and/or
(f) optionally amplifying and/or sequencing the phosphorothioate-labeled nucleic acid fragment, and/or
(g) mapping the phosphorothioate-labeled nucleic acid fragment onto a genomic map corresponding to a source of the nucleic acid.

In some embodiments, the ddNTP is dideoxycytidine.

In some embodiments, the treating of step (b) is enzymatically, chemically and/or mechanically treating.

In some embodiments, the polymerase is DNA polymerase I.

In some embodiments, the nucleic acid is DNA.

In some embodiments, the nucleic acid modification is a phosphorothioate modification, optionally wherein said nucleic acid modification is converted into a single-stranded nick using iodine.

In some embodiments, the nucleic acid modification is a methyl5C modification, optionally wherein said nucleic acid modification is converted into a single-stranded nick using TET or TDG enzyme that converts a methyl5C to an abasic site and an AP endonuclease that converts abasic sites to single-stranded nicks capable of nick translation.

In some embodiments, the nucleic acid modification is a DNA damage modification, optionally wherein said DNA damage modification is 8-oxoguanine, optionally wherein said nucleic acid modification is converted into a single-stranded nick using FAPY glycosylase.

In some embodiments, the nucleic acid modification is a nucleic acid secondary structure.

In some embodiments, the phosphorothioate-labeled nucleic acid fragment is 100-1000 nucleotides in length, optionally 100-500 nucleotides in length.

Another aspect provides a method for detecting and mapping one or more modifications in a DNA sample comprising
(a) incubating a DNA sample with DNA polymerase I and dideoxycytidine under conditions sufficient to fill in and/or block existing single-stranded nicks in the DNA sample,
(b) treating the DNA sample to convert existing DNA modifications into single-stranded nicks, optionally wherein said treating is enzymatically, chemically or mechanically treating, thereby generating nicked DNA,
(c) incubating the nicked DNA with alpha-thio-dNTPs and DNA polymerase I under conditions sufficient to generate phosphorothioate-labeled DNA fragments through a process of nick translation/strand displacement, optionally wherein said fragments are at least 100-500 nucleotides in length,
(d) incubating the DNA sample with nuclease P1 or an endo- or exo-nuclease that does not cleave phosphorothioate-labeled DNA fragments,
(e) isolating the phosphorothioate-labeled DNA fragments, optionally by ethanol precipitation or column chromatography,
(f) amplifying and sequencing the phosphorothioate-labeled DNA fragments to generate sequencing reads and
(g) mapping the sequencing reads onto a genomic map of the source of the DNA sample.

In some embodiments, the DNA modification is a phosphorothioate modification, optionally wherein said nucleic acid modification is converted into a single-stranded nick using iodine.

In some embodiments, the DNA modification is a methyl5C modification, optionally wherein said nucleic acid modification is converted into a single-stranded nick using TET or TDG enzyme that converts a methyl5C to an abasic site and an AP endonuclease that converts abasic sites to single-stranded nicks capable of nick translation.

In some embodiments, the DNA modification is a DNA damage modification, optionally wherein said DNA damage modification is 8-oxoguanine, optionally wherein said nucleic acid modification is converted into a single-stranded nick using FAPY glycosylase.

In some embodiments, the DNA modification is a nucleic acid secondary structure.

Another aspect provides a method for detecting and mapping one or more nucleic acid lesions in a nucleic acid sample comprising
(a) incubating a nucleic acid sample with a polymerase and alpha-thio-dNTPs under conditions sufficient to generate a phosphorothioate-labeled nucleic acid fragment,
(b) removing unlabeled nucleic acids under conditions that specifically degrade said unlabeled nucleic acids and do not degrade the phosphorothioate-labeled nucleic acid fragment,
(c) optionally isolating or purifying the phosphorothioate-labeled nucleic acid fragment, and/or
(d) optionally amplifying and/or sequencing the phosphorothioate-labeled nucleic acid fragment, and/or further optionally mapping the phosphorothioate-labeled nucleic acid fragment onto a genomic map corresponding to a source of the nucleic acid sample.

In some embodiments, the polymerase is DNA polymerase I.

In some embodiments, the nucleic acid is DNA.

In some embodiments, the phosphorothioate-labeled nucleic acid fragment is 100-1000 nucleotides in length, optionally 100-500 nucleotides in length.

In some embodiments of any of the foregoing aspects, the nucleic acid or DNA is present in a sample, wherein the sample is prepared from and/or contains cells or tissue.

Another aspect provides a kit comprising alpha-thio-dNTPs, ddNTP, optionally wherein the ddNTP is or comprises dideoxycytidine, a polymerase, and optionally a buffer.

In some embodiments, the kit further comprises iodine.

In some embodiments, the kit further comprises FAPY glycosylase.

In some embodiments, the kit further comprises TET or TDG enzyme capable of converting a methyl5C to an abasic site.

In some embodiments, the kit further comprises an AP endonuclease capable of converting an abasic site to a single-stranded nick suitable as a substrate for nick translation.

In some embodiments, the kit further comprises an enzyme capable of converting a DNA damage lesion to a single-stranded nick.

In some embodiments, the kit further comprises an enzyme capable of removing a sugar residue from a nucleic acid.

In some embodiments, the kit further comprises a hydroxyl radicals or a chemical capable of generating hydroxyl radicals.

In some embodiments, each component of the kit is housed in a separate container.

These and other aspects and embodiments of this disclosure will be described in greater detail herein.

BRIEF DESCRIPTION OF DRAWINGS

FIG. 5: Ligation of cDNA with Linker 2. Upper: Sequence and structure of Linker 2. The 3'-propyl "spacer" blocks self-ligation during the reaction. N, randomized nucleotides. As shown, Linker 2 may have the sequence of 5'-phosphate-TGAAGAGCCTAGTCGCTGTT-CANNNNNNCTGCCCATAGAG-propyl-3' (SEQ ID NO:4). In other embodiments, Linker 2 may have the sequence of 5'-phosphate-TGAAGAGCCTAGTCGCTGTTCANNNNNNCTGCC-CATAGAGC-propyl-3' (SEQ ID NO:5). Middle: Schematic of Linker 2 self-hybridized to form a hairpin structure at its 5' end. Lower: Using T4 DNA ligase, this uniquely-designed hairpin/splint oligodeoxynucleotide linker provides for >95% and in some instances >96% ligation efficiency with the 3'-end of the cDNA. Synthetic oligos between 50 and 80 nucleotides in length were tested to simulate ligation of Linker 2 to full- and half-length tRNA starting material. Removal of 50-fold excess of Linker 2 using deadenylase and recJ is nearly stoichiometric. Levels of excess, unligated Linker 2 were unable to be detected by Bioanalyzer. In the absence of ligase, no ligation product was observed (i.e., peak on the Bioanalyzer trace corresponded to the length of the cDNA, data not shown). In the presence of 20-fold or 50-fold excess linker, the peak shifted to the right, indicating formation of the ligation product (data not shown).

FIG. 6: Exemplary forward and reverse PCR primers used to incorporate sample-identifying barcodes (for multiplexing applications) and Illumina anchor sequences are illustrated. Both primers contain regions that are reverse complementary to Linkers 1 and 2 on the cDNA, as indicated and also underlined. X represents defined barcode sequences that enable multiplexing of samples. The 5' portion of the primers contain sequences (shown as bolded) that are compatible with Illumina anchor sequences. As illustrated, primer 1 has the sequence of (SEQ ID NO: 6)
5'-AATGATACGGCGACCACCGAGATCTACA-C-XXXXXX-ACACTCTTTCCCTACACGACGCTCTTCCGATCT-TGAACAGCGACTAGGCTCTTCA-3', and primer 2 as the sequence of (SEQ ID NO: 7)
5'-CAAGCAGAAGACGGCATACGAGAT-XXXXXX-CGGTCTCGGCATTCCTGCTGAACCGCTCTTCCGATCT-GTCCTTGGTGCCCGAGTG-3'.

A color version of the Figures is being filed along with a gray-scale version. Reference may be made to the color version where color is used to distinguish and/or highlight information in the Figures.

DETAILED DESCRIPTION

This disclosure provides various methods and products relating to detection, quantification and sequencing of nucleic acids such as but not limited to RNA. This disclosure further provides various methods and products relating to universal detection of nucleic acid features (e.g., mutations, modifications, etc.). The various aspects and embodiments of this disclosure are discussed in greater detail below.

RNA Sequencing Methods for Absolute Quantification of RNA Molecules

This disclosure provides, in part, methods that enable one skilled in the art to perform RNA sequencing in which the abundances (i.e., copy numbers) of different RNA molecules can be compared directly in the same sample. Unlike other RNA sequencing methods, which allow only relative quantification of changes in the levels of RNA molecules between different samples, the method described here enables a direct, linear correlation between the sequencing read counts and the number of copies of all RNA molecules within a single sample. This allows quantitative definition of landscape of RNA molecules in a cell or tissue at any given moment. This process can be applied to RNA from any source, with multiplexing to accommodate many samples, and it can be used to investigate gene expression, RNA metabolism, RNA stability, RNA therapeutics, and any other problems related to quantitative analysis of RNA molecules.

Figure 1:
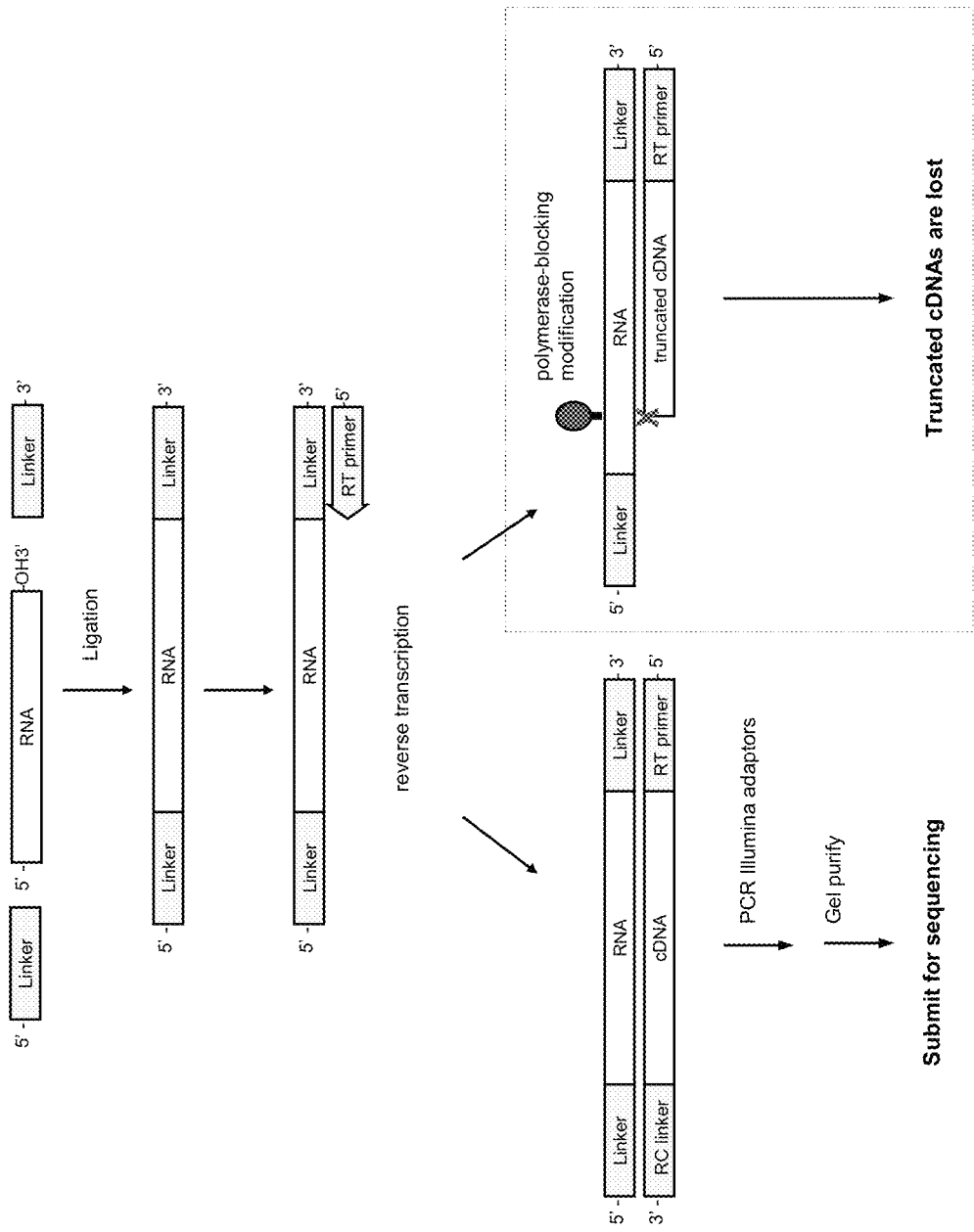
FIG. 1: Traditional RNA sequencing involves simultaneous ligation of oligonucleotide linkers to the 3'- and 5'-ends of RNA molecules (such as tRNAs). Such ligation may be carried out using a ligase enzyme such as but not limited to T4 RNA ligase I. This may be followed by hybridization to an RT primer and then reverse transcription, PCR, typically with concomitant RNA degradation, and purification of cDNA for NGS sequencing (see left path). The resulting sequence information is highly biased by $10^3$-fold variation in ligase efficiency due to sequence variation at the ends of each RNA molecule and by fall off of the reverse transcriptase when it encounters modified nucleotides in RNA.

As shown in FIG. 1, the current RNA sequencing technology works by first attaching defined-sequence nucleic acid (e.g., DNA) oligonucleotides to each end of an RNA molecule using RNA ligase enzymes. A reverse transcriptase enzyme is then used to create a complementary copy of the RNA molecule (e.g., a complementary DNA, or cDNA), followed by polymerase chain reaction (PCR) amplification of the cDNA molecule. The amplified cDNAs are then subjected to NGS for identification and quantification of all of the original RNA molecules in a sample such as a cell. Thus, current RNA sequencing methods allow analysis of relative changes in the levels of RNA molecules between two or more conditions, with the resulting fold-change data providing insights into how a condition affects changes in the levels of different RNA molecules.

These methods cannot however be used for absolute quantification of RNA molecules, in which the levels of different types of RNA transcripts are compared in the same sample of RNA. For example, there are ~30-55 different types of transfer RNAs (tRNAs) in most types of prokaryotic cells such as bacteria. Eukaryotic cells, including yeast and human cells, can have up to hundreds of different transfer RNAs. tRNAs represent the adaptor molecules that read the genetic code in messenger RNAs (mRNAs) and carry the corresponding amino acid for synthesis of the protein encoded by the mRNA. The level of each type of tRNA is thought to reflect the translational needs of the cell at any given moment, with some specific types of tRNA occurring at very low levels while other types potentially present at orders-of-magnitude higher levels.

There are two reasons why current RNA sequencing techniques cannot be used for absolute quantification of RNA molecules. First, the attachment of oligonucleotide linkers to each end of an RNA molecule before reverse transcription results in the loss of information about some RNA molecules when the reverse transcriptase falls off the RNA due to an error in processivity of the enzyme or due to an encounter with some types of modified nucleosides. Regarding the latter, the cells in each type of organism contain 25-50 or more chemical modifications of the canonical A, G, C and U nucleotides in RNA.[1,2] Some of these modifications block the polymerase activity during reverse transcription, so that the enzyme falls off the RNA molecule before completely copying the molecule through to the other end. Such failure sequences do not possess the second PCR linker, so they cannot be amplified and thus fail to appear in the final sequencing results (FIG. 1, boxed).

A second problem is that the ligase enzymes used for RNA sequencing vary in their efficiency by more than $10^3$-fold due to differences in the last two nucleotides at each end of the RNA molecule.[3-5] This variation in linker ligation efficiency manifests as $10^6$-fold variation in the read counts from RNA sequencing applied to tRNA molecules.[6] There is thus no predictable or direct correlation between sequencing read counts and the number of copies of an RNA molecule in a sample analyzed by current RNA sequencing methods.

As described herein, to satisfy the need for absolute quantification in RNA sequencing analyses, an RNA sequencing method has been developed that enables a direct, linear correlation between the sequencing read counts and the number of copies of all RNA molecules within the same sample. The method is detailed in FIG. 2. In one exemplary embodiment, the method may be used to detect and measure tRNA molecules.

This process may involve the following steps: (1) dephosphorylate purified RNA, in some instances consisting of all RNA molecules including for example all RNA molecules less than 200 nt in length ("small RNA"), which includes tRNAs; (2) ligate a dideoxycytidine-ended oligodeoxynucleotide linker with two randomized nucleotides at the 5'-end (Linker 1) to the dephosphorylated RNA using for example T4 RNA ligase, which results in >91% ligation efficiency; (3) reduce the levels of RNA modifications using an AlkB enzyme which may be a mutant AlkB enzyme or it may be a mixture of AlkB enzymes having differing fidelities and/or susceptibilities to modifications; (4) remove excess Linker 1 by treating the sample with for example deadenylase to remove a ligase-mediated intermediate and then degrading Linker 1 for example with the 2'-deoxyribonuclease Rec J; (5) reverse transcribe the linker-ligated RNA into cDNA using a primer complementary to Linker 1 and reverse transcriptase; (6) degrade the RNA template for example by alkaline hydrolysis; (7) ligate a uniquely-designed hairpin/splint oligodeoxynucleotide linker (Linker 2) to the cDNA molecules using for example T4 DNA ligase; (8) remove excess Linker 2 for example by deadenylation and Rec J treatment as described in step #4; and (9) ligate standard NGS sequencing linkers by PCR followed by sequencing using standard NGS platforms.

As a method for absolute quantification of RNA molecules in the same sample, which is not possible for existing methods, this RNA sequencing method involves an new and nonobvious combination of RNA- and DNA-manipulating enzymes and uniquely structured oligodeoxynucleotide linkers to process a mixture of RNA molecules (i.e., prepare an RNA library) for subsequent sequencing by standard NGS methods. The inventive features of these methods include: (1) uniquely designed oligodeoxynucleotide linkers and optimized reaction conditions that enhance the efficiency of the RNA and DNA ligase enzymes to >91%; (2) unique combinations of enzymes (deadenylase, Rec J) that allow removal of excess linkers without harming the RNA template or cDNA product, thus enhancing the efficiency of subsequent enzymatic reactions; and (3) the ligation of the 5' linker (Linker 2) after the reverse transcription step, which avoids loss of RNA molecules by fall-off of the reverse transcriptase. This novel and nonobvious combination of reagents and conditions allows deep-sequencing analysis of the RNA molecules such that the sequencing read count for each type of RNA is directly and linearly correlated with the number of copies that RNA sequence. This method can be applied by researchers in the form of a kit in many fields of academic, regulatory or industrial science using any type of synthetic or natural RNA from any organism, such as viruses, bacteria, parasites, yeast, and mammalian and human cell and tissues.

This RNA sequencing method has been reduced to practice in at least three applications: (1) with standard mixtures containing 5 RNA oligos of varying lengths and abundances to determine the extent of length-dependent biases and confirm the linearity of the sequencing method for RNAs between 25 and 80 nucleotides, (2) with an equimolar mixture of microRNA standards to determine the extent of sequence-dependent biases on quantification, and (3) with DNA from *Mycobacterium bovis* BCG bacteria to demonstrate the landscape and how the landscape changes when the cells are subjected to the stress of nutrient deprivation.

The present disclosure provides a widely applicable methodology to quantify expressed intracellular RNA species, including tRNA isoacceptors and tRNA fragments, using next generation sequencing (NGS). This novel method for NGS library preparation can efficiently capture small RNA sequences without bias for length or sequence and quantitatively convert these sequences into cDNA by reverse transcription. The resulting cDNA is then PCR amplified and sequenced using paired-end high-throughput sequencing. Aligned output reads can be used to determine the absolute abundance of expressed small RNAs including both full-length and fragment tRNA isoacceptors.

Existing methods for quantifying RNAs by sequencing have mainly focused on mRNA (transcriptional profiling) using either total RNA or enriched mRNA as starting materials. mRNA is considerably easier to sequence by NGS methods because relative to tRNA, it is less structured and it contains fewer RNA modifications, both of which hamper cDNA synthesis from tRNA. For example, existing methods for mRNA sequencing involve simultaneous ligation of 5' and 3' adapters followed by reverse transcription and PCR amplification. In contrast, in the present disclosure, only the 3' linker is ligated to the RNA starting material prior to reverse transcription. This is done to reduce loss of templates that form truncated cDNA due to the presence of polymerase-blocking modifications or secondary structures (FIG. 1). Furthermore, the 3'-linker is designed with two randomized NN nucleotides in the 5'-end to maximize capture of all RNA species in the starting material by eliminating sequence-dependent ligation biases.[3-5]

An example of an alternate approach for tRNA sequencing has been reported. It incorporates an enzymatic tRNA demethylation step prior to cDNA generation to minimize the effect of polymerase-blocking modifications, uses a template-switching reverse transcriptase in order to obviate the need for linker ligation, and employs a cDNA circularization strategy prior to amplification.[8] This reported method however does not take as rigorous an approach to quantitation as the methods disclosed herein. In both the reverse transcription and circularization steps, their method does not address known sequence-dependent biases in the activities and efficiencies of the enzymes.[9] For example, the circularization efficiency of CircLigaseII, the commercially available ssDNA ligase used in the prior method, is known to vary depending on identity of the two terminal nucleotides.[9] In the context of measuring the composition of the expressed tRNA pool, such sequence-dependent biases will skew the capture of isoacceptors carrying "preferred" sequences and cannot be relied up on to provide accurate quantitation of the full tRNA or small RNA landscape.

In the present disclosure, by contrast, every step and parameter of the method, including adapter sequences, stoichiometries, and enzymatic reaction conditions, have been designed, tested, and optimized to either quantitatively capture all sequences or be free from sequence-dependent biases. To start, the 3'-Linker 1 is designed with two randomized nucleotides at the 5'-end to minimize ligation differences between varied sample sequences. Indeed, using this approach, it is demonstrated that >91% of starting sequences are ligated with a 3'-end Linker 1 by Bioanalyzer analysis. Reverse transcription proceeds after the first ligation step and demethylation. To avoid sequence biases reported with the template-switching reverse transcriptase enzyme used by others,[8] a high-processivity, high-accuracy, thermostable, commercially-available reverse transcriptase was selected, although it was also found that a mixture of enzymes with slightly differing fidelities and susceptibilities to modifications could also be used in this step. The 5'-Linker 2 is designed to have a hairpin with a six-nucleotide NNNNNN overhang that is complementary with the 3'-end of the cDNA. This structure brings the 5'-end of the Linker in close proximity to the 3'-end of the target cDNA to maximize ligation efficiency. With these optimizations, there is nearly complete conversion of the cDNA to cDNA+5' adapter by Bioanalyzer.

An unbiased RNA sequencing method has many commercial applications in basic and applied research, biomedical diagnostics, drug development, and any other biological or biomedical application requiring knowledge of RNA levels. All commercial applications would derive from a basic kit containing DNA oligos, buffers, and enzymes to allow high-throughput quantification of RNA and RNA fragments in any size range.

Examples of applications of the RNA sequencing method of this disclosure and variations thereof include:

RNA quantification—The basic methodology is applicable to generating RNA profiles in samples of cultured cells and tissues, including bodily fluids and excretions (urine, saliva, blood, feces). These RNA profiles can be used in a number of research applications related to diagnosis of infectious disease, quantification of gene expression, quantification of microRNAs or non-coding regulatory RNAs, measurement of RNA stability, analysis of RNA processing, and any other application requiring quantitative analysis of RNA.

Identification and quantification RNA modifications—There is increasing evidence that RNA modifications have important functions in RNA processing, RNA stability, and the regulation of translation. This methodology would find use in identifying and quantifying RNA modification sites as reverse transcriptase "fall-off" sites when the AlkB treatment (e.g., mutant AlkB treatment) is omitted or as bypass mutagenesis sites when a modification induces a misincorporation. There is great value in defining maps of the locations of modified nucleotides in different RNA molecules, all in the same sample, as well as changes in the maps as a function cell state and stress.

RNA fragmentation analysis—Recent studies have revealed novel mechanisms of control of gene expression and RNA stability by small RNA fragments generated from larger functional RNAs such as tRNA, mRNA and rRNAs. The present methodology is able to quantify all RNA fragments in a sample, to quantify the fragments in relation to the parent RNA species, and to define the location of the fragmentation reaction. This would provide invaluable insights into the biological and medical impact of small regulatory RNA species.

Study of the biogenesis of functional RNA and RNA decay—Primary RNA transcripts undergo various processing events including splicing, joining of different units, trimming, and circularization prior to maturation. The present methodology is able to quantify intermediary RNA fragments in a sample and to quantify these intermediates in relation to the mature RNA species, and to define the localization of intermediates. This would provide invaluable insights into the biological and medical impact of small regulatory RNA species.

RNA biomarker discovery—This methodology can generate the landscape of all RNA molecules in a cell that can be compared against a known landscape that is from specific disease or condition, thus informing a biomarker of this disease or condition. This special biomarker can be used for predictive of prognosis and/or diagnosis of the disease or condition.

Mapping DNA Modifications and DNA Damage at Single-Nucleotide Resolution Across Genomes This disclosure further provides widely applicable methods for quantitative profiling, localizing or mapping of nucleic acid (e.g., DNA) modifications, damage or structures at single-nucleotide resolution in any type of nucleic acid (e.g., DNA) and across entire genomes from any organism. These maps can be related to other DNA structures and genome architecture, and also provide a means to identify the biological source of the DNA. This process can be applied to any DNA modification or DNA structure that exists as a single-strand break or that can be converted into a single-strand break, including, among other examples, (1) DNA nicks arising during natural DNA metabolism, such as damage, repair, modification, replication, transcription and other processes, and (2) intentional conversion of these and other DNA and chromatin features into DNA nicks by chemical, mechanical or enzymatic means. The resulting profile or map of the DNA nicks across a genome provides information about the genomic location of the feature, the frequency of a feature at any specific site in the genome, and changes in the locations and quantities of DNA features as a function of cell stress, cell type, disease state or any other situation. The method will find wide application in many fields of biological and biomedical research and development in academia and in the clinic.

The ability to localize DNA damage and DNA repair processes throughout an entire genome, to define regions that are hotspots for damage or that show different rates of repair, which may be strongly associated with the frequency of mutations causing disease such as cancer, diabetes and many others has many applications. DNA sequencing is being used to localize sites of DNA damage and repair in the genome. For example, following fragmentation of genomic DNA, antibodies against specific kinds of DNA damage can be used to affinity purify DNA fragments containing the damage, with the fragments subjected to standard DNA sequencing to crudely localize the damage in the genome. However, this is imprecise at best.

DNA sequencing technology has also been used to define the locations of the m5C modifications—the methylome—in specific genes in a genome and the patterns of modification that correlate with gene expression patterns in different cells and tissues. One method for mapping m5C in genomes involves the selective conversion of C but not m5C to uracil (U) by reaction with bisulfite. Subsequent sequencing then reveals the location of all m5Cs as a normal C, while U's arising from unmodified C's are sequenced as thymidine (T).

The problem with the current use of DNA sequencing technologies for mapping DNA features such as damage and modifications across a genome, however, is that each method is uniquely designed for only one feature. For example, bisulfite sequencing can only be applied to methylome mapping. There are no universal methods for mapping different types of DNA modifications or damage products.

This disclosure provides such universal methods.

Figure 10:
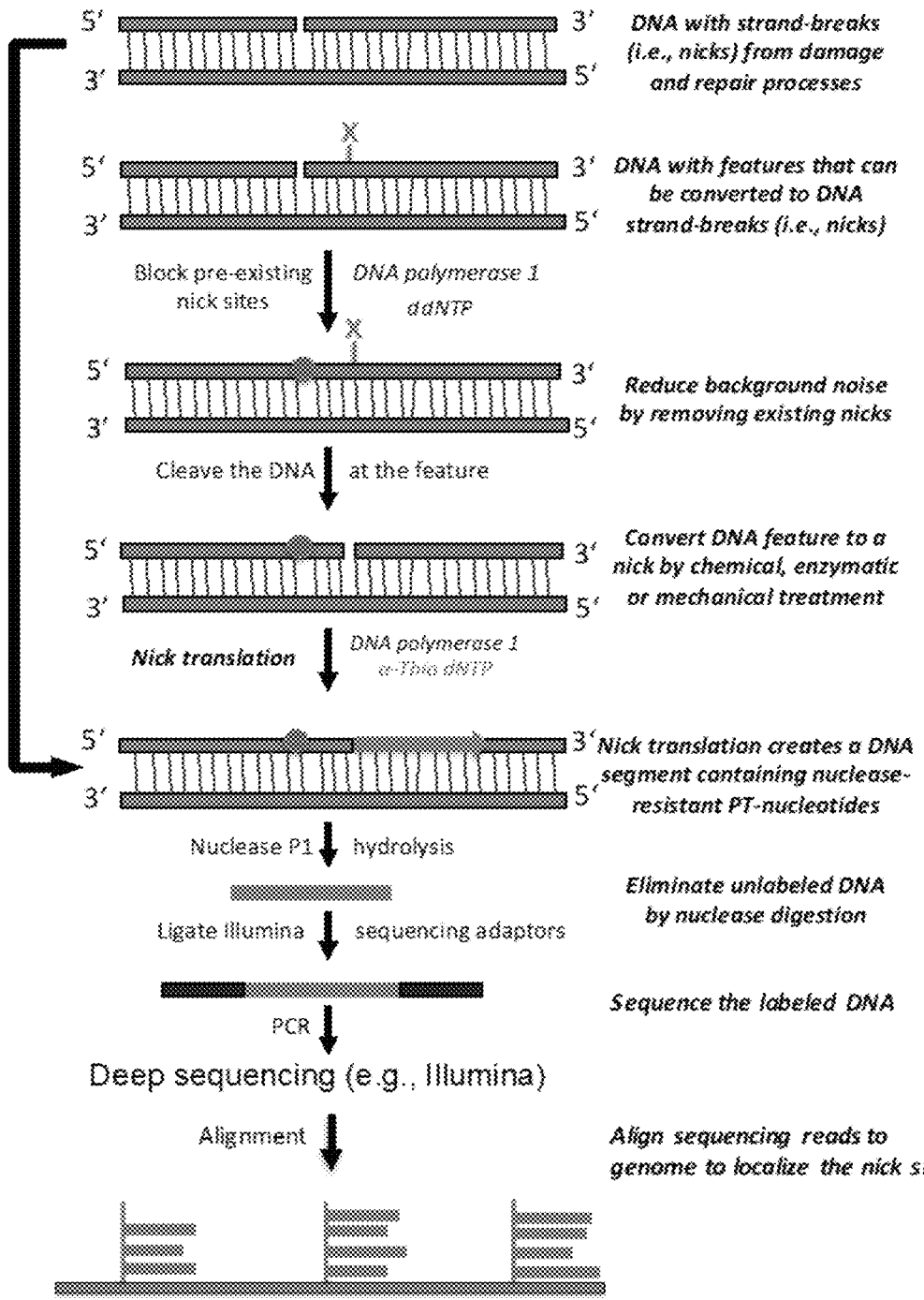
FIG. 10: The Nick-seq™ method.

The Nick-seq™ sequencing method has been developed for single-nucleotide-resolution, genome-wide localization of any kind of DNA feature that can be converted to a DNA strand-break (i.e., nick). The method is illustrated in FIG. 10.

Specifically, the novel process may involve the following steps for DNA with modifications and features that need to be converted into nicks (for DNA already containing nicks of interest, proceed to step 3): (1) treat the purified DNA with DNA polymerase I and ddNTP, such as dideoxycytidine, to block existing DNA nicks; (2) treat the DNA samples (e.g., enzymatically, chemically, mechanically) to create DNA nicks at features of interest (e.g., DNA modifications, DNA damage); (3) label the new DNA nicks by nick translation (i.e., DNA strand displacement with α-thio-dNTPs) by DNA polymerase 1 to create phosphorothioate-containing DNA fragments (PT-DNA) starting at nick sites and extending several hundred nucleotides; (4) remove the original, unlabeled DNA by digestion with nucleases, such as nuclease P1, a combination of RecJ and Exonuclease III, or other exo- or endo-nuclease(s), which do not cleave PT-containing DNA; (5) purify the PT-DNA fragments for example by ethanol precipitation or column chromatography; (6) amplify and optionally sequence the DNA for example using standard deep-sequencing techniques; and optionally (7) map the deep-sequencing reads onto the original DNA or genome by standard informatics methods. The sites of the original DNA nicks will be evident as the 5'-most nucleotides of the sequenced PT-DNA fragments.

As a method for mapping DNA features at ultra-high (i.e., single-nucleotide) resolution, this Nick-seq™ sequencing method relates to the ability to extend (or translate) DNA nicks with DNA polymerase 1. Nick translation has been used to label sites containing DNA nicks. The methods provided herein differ from classical nick translation, at least in part, by transforming the DNA sites of interest into nuclease-resistant DNA fragments (i.e., PT-DNA). This transformation allows deep-sequencing analysis of the DNA fragments and enhances the signal-to-noise ratio of the sequencing by destroying the bulk of the unlabeled genomic DNA. This method can be applied by researchers in the form of a kit in many fields of academic, regulatory or industrial science using any type of DNA or organism containing DNA, such as viruses, bacteria, parasites, yeast, mammalian cells, and human cells. Further, the method can be applied to any kind of DNA modification, DNA damage, enzymatic cleavage site in DNA, or any other DNA-related feature that can be converted to a DNA nick. The methodology provides unprecedented access to information about the genomic locations of DNA features, as well as a means to identify the source of the nick-containing DNA, such as organisms in complex environments and the microbiome. This has not been possible heretofore with existing methods.

Figure 11A:
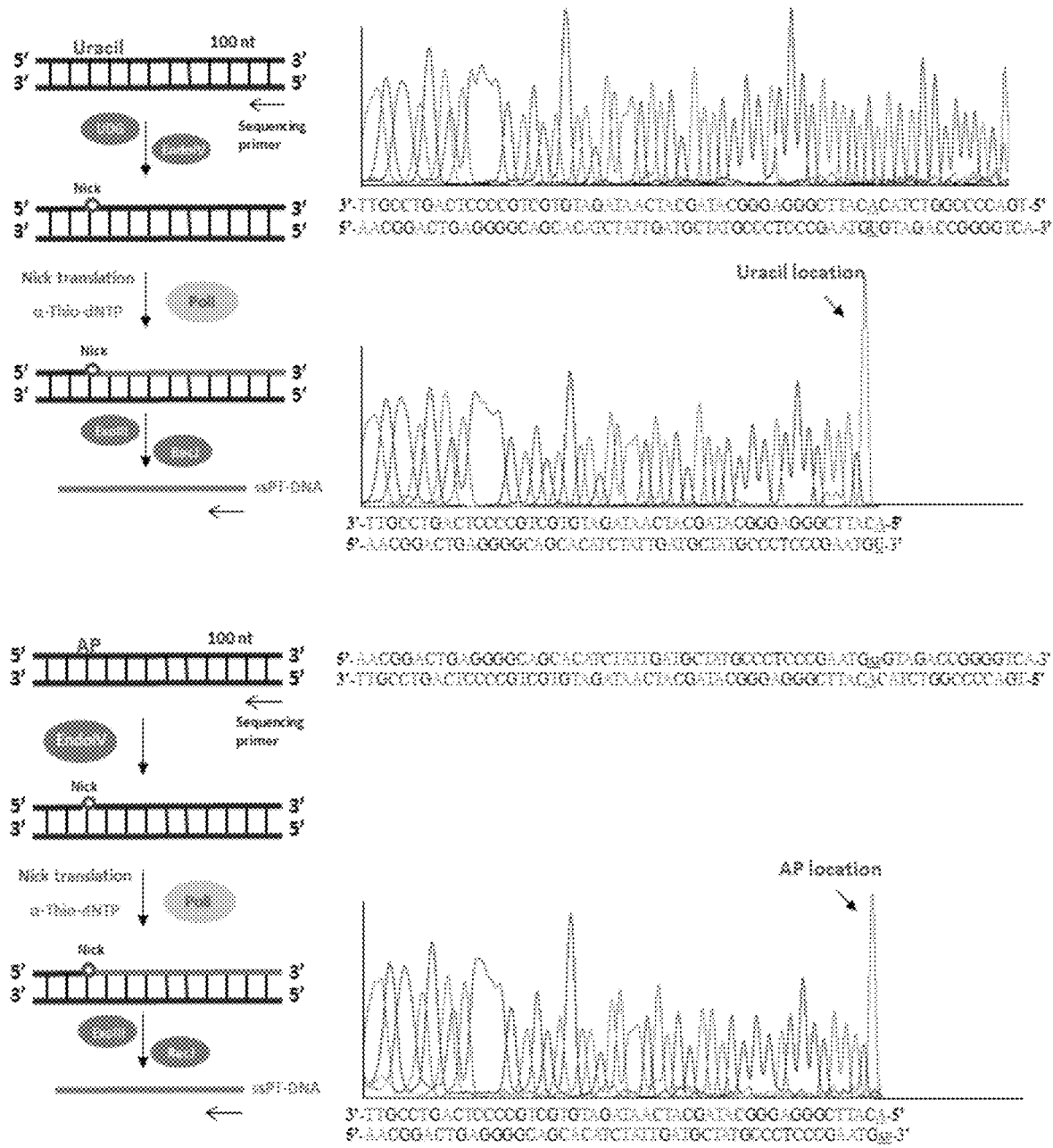
FIGS. 11A and 11B: Application of the Nick-seq™ methodology: Map of DNA damage and modification sites in DNA oligonucleotides. The sequences in the Figures are as follows: For FIG. 11A, the sequences correspond to SEQ ID NOs: 8, 9, 10, 11, 12, 8, 10, 13, from top to bottom. For FIG. 11B, the sequences correspond to SEQ ID NOs: 14-21, from top to bottom.
Figure 11B:
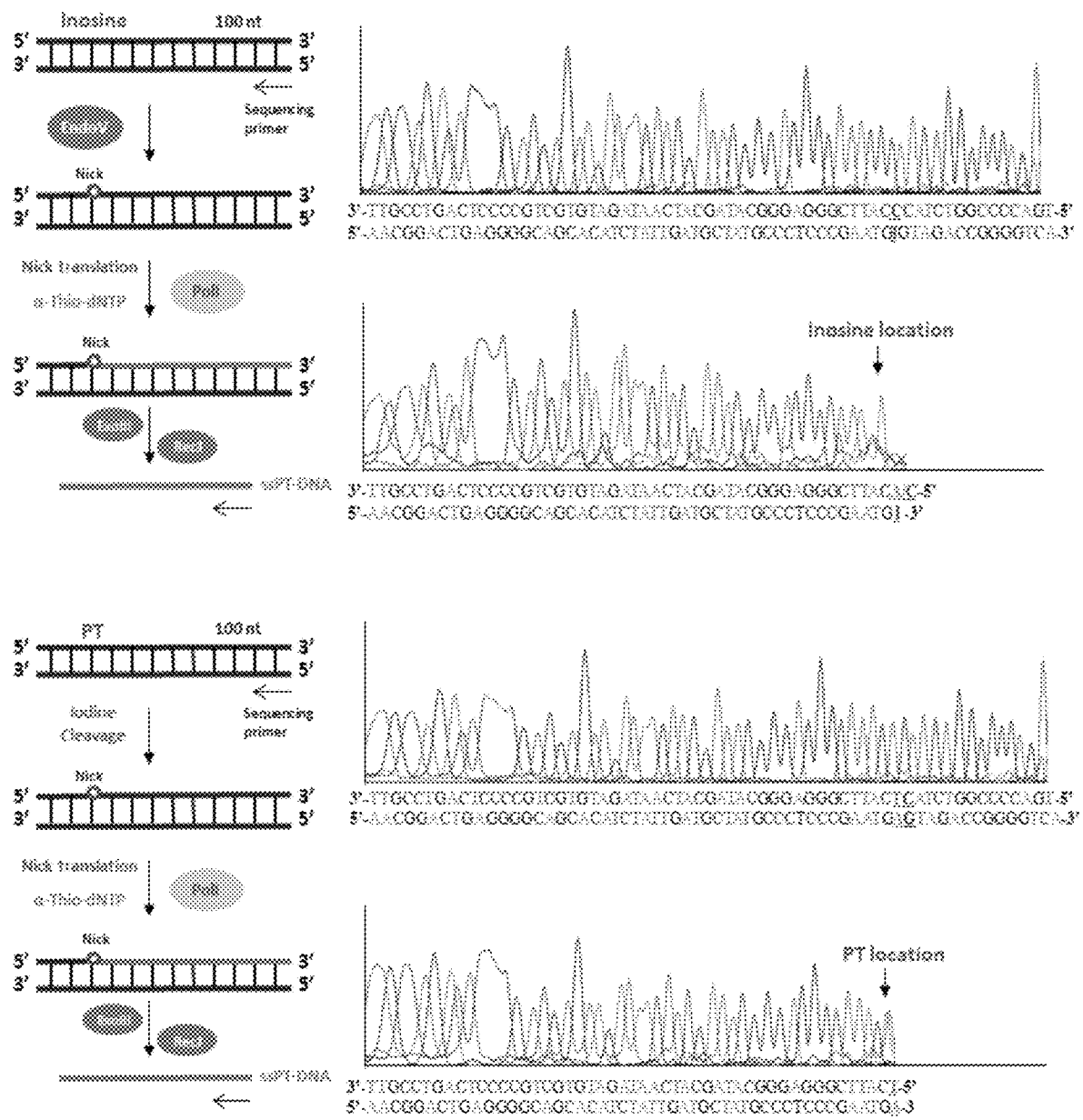

The specificity and sensitivity of the Nick-seq™ method has been demonstrated using synthesized DNA oligos (FIGS. 11A and 11B). Here DNA containing a damage/modified site, including uracil, inosine, AP site and phosphorothioate modification, were treated with enzymes or chemicals that can specifically convert corresponding damage/modification sites to DNA strand breaks. Applying the Nick-seq™ method (FIGS. 11A and 11B) and Sanger sequencing, the converted nick site was determined by a sharp stop in the Sanger sequencing chromatogram, indicating that the 5' end of PT exactly corresponded to the nick site.

Figure 12:
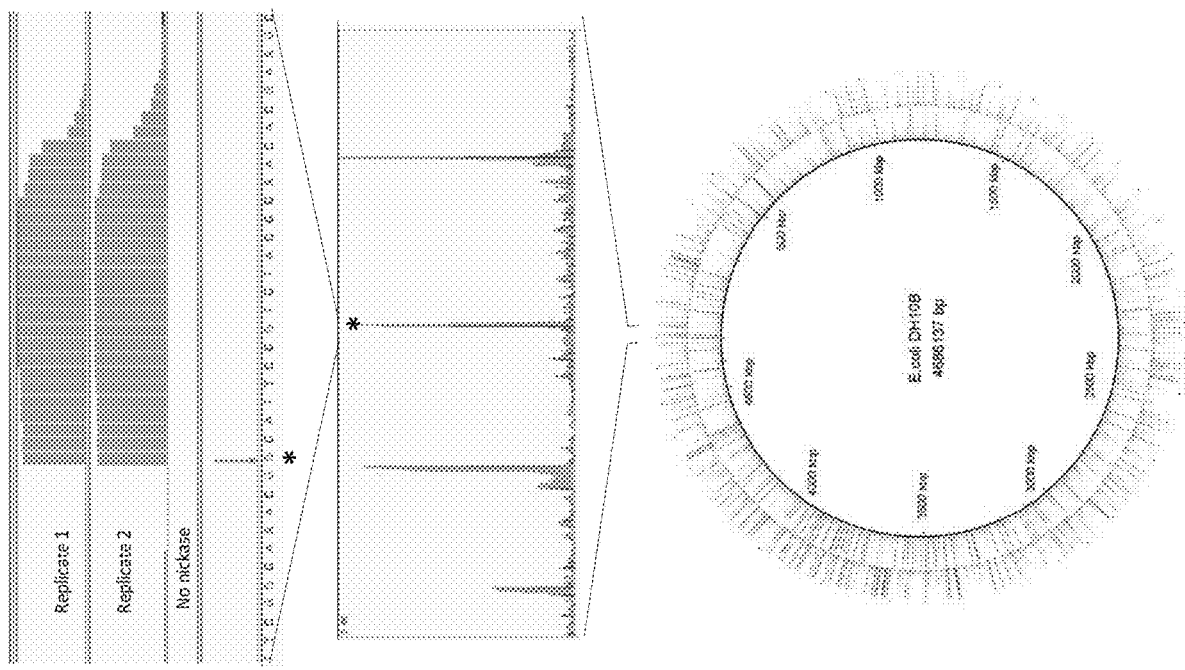
FIG. 12: Application of the Nick-seq™ methodology: Genomic map of Nb.BsmI nickase cleavage sites in the *E. coli* genome. The sequence corresponds to SEQ ID NO: 22.

The specificity and sensitivity of the Nick-seq™ method has also been demonstrated in a bacterial genome (FIG. 12). Here DNA was purified from *E. coli* DH10B and treated with the sequence-specific endonuclease Nb.BsmI (New England Biolabs). This single-strand nicking enzyme cuts only at NGACATTC sequences, of which there are 1324 in the *E. coli* DH10B genome. Applying the Nick-seq™ method (FIG. 12), 1321 of 1324 Nb.BsmI sites were detected, with an average of 813 read counts per site (a 50-read-count threshold was set to reduce noise) and 5 false-positive sites. The fact that only 0.4% of the signals above noise were detected as non-specific cleavage sites points to the very high specificity of the method. It is also possible that the 5 false-positive cleavage sites represent "star" activity or sloppiness for the Nb.BsmI.

Figure 13:
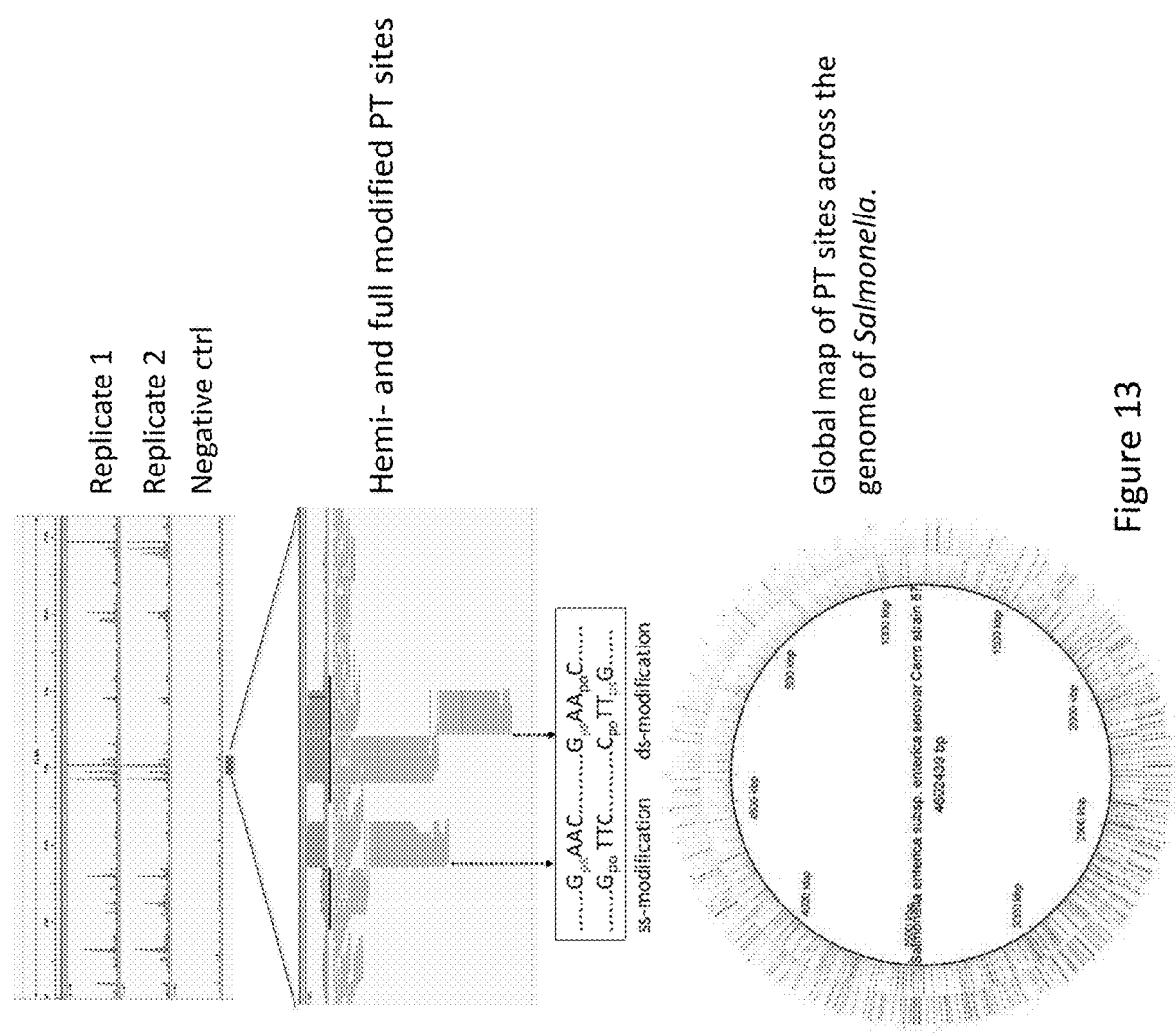
FIG. 13: Application of the Nick-seq™ methodology: Genomic map of DNA phosphorothioate modification sites in the *Salmonella* genome.

The specificity and sensitivity of the Nick-seq™ method for mapping PT modification in a bacterial genome (FIG. 13) has also been demonstrated. Here DNA was purified from *Salmonella enterica* and treated it with iodine solution to specifically cleave the PT modification sites and produce a strand break. Applying the Nick-seq™ method, 9378 sites were detected at $G_{PS}AAC$ or $G_{PS}TTC$, two-times more than that detected by SMRT sequencing[13]. In addition, 24 $G_{PS}ATC$ and 137 $G_{PS}TAC$ sites were also detected at lower abundance than $G_{PS}AAC/G_{PS}TTC$. These sites were not detected by other methods. These results show that that Nick-seq™ method is more sensitive than others to detect rare modification events.

The present disclosure provides a widely applicable method to identify the genomic locations of DNA modifications, damage and structures that can be converted to strand-breaks. The methodology labels these sites nuclease-resistant modifications that allow destruction of the unlabeled genome with a nuclease and subsequent deep-sequencing of the protected fragments in which the 5'-end maps the location of the nick of interest. This process allows one to map any kind of DNA feature that can be converted to a nick, in DNA of virtually any size, from oligonucleotides to genomes, and in DNA from any source. Existing methods to map DNA damage and modifications across genomes, such as bisulfite sequencing to locate methylation modifications, are limited to a specific modification and cannot be applied to other modifications. Unlike the present method that allows single-nucleotide resolution and high sensitivity, existing methods for mapping strand-breaks, such as 3'-terminal labeling with biotin or fluorescent molecules by terminal transferase (TdT) or DNA polymerase, are highly insensitive and most do not provide information about the precise location in the genome, with resolution limited to very crude estimates of the position in large DNA molecules or regions of the genome. For those high-resolution genome mapping methods that provide single-nucleotide resolution of DNA features, they also suffer from reliance on computational predictions or specialized immunoprecipitation steps that limit the methods to specific types of DNA features. For example, a computational approach has been developed to map DNA structures across genomes by comparing DNA sequenced-based structural predictions to a computed likelihood of DNA cleavage by hydroxyl radicals (ORChID: •OH Radical Cleavage Intensity Database) based on an empirical collection of DNA cleavage patterns from small DNA fragments.[10] While this method can help our understanding of how DNA sequence determines the locations of protein-binding sites and other biologically important structural features of DNA, this method approach identifies predicted structures and not true structures. In contrast, the Nick-seq™ method would allow one to generate genome-wide maps of hydroxyl radical cleavage patterns that would reveal the true structures present in any genome.

Another method to map sites of DNA repair across a genome has been recently developed. This method intends to map sites of nucleotide excision repair (NER) in the human genome, as a tool to better understand mechanisms governing NER and to correlate defects in NER with mutations that cause disease.[11] However it requires two immunoprecipitation steps to enrich for the repair sites prior to deep-sequencing, so the method is applicable only to NER-related studies. The Nick-seq™ method would be immediately and directly applicable to the analysis of NER repair sites, without the need for immunoprecipitation steps.

Another example of a method to map DNA damage across a genome involves the single-strand DNA (ssDNA)-associated protein immunoprecipitation followed by sequencing (SPI-seq).[12] Here, sites of single-stranded DNA are enriched by immunoprecipitation of a DNA single-strand-binding protein. The sites of SS DNA are then defined by deep-sequencing. Again, the Nick-seq™ method can be applied to map regions of single-strand DNA in a genome without the need for the immunoprecipitation step that adds sequence noise as well as time and expense to the method.

Thus, certain methods of this disclosure may be carried out in the absence of immunoprecipitation or other enrichment steps, in contrast to various existing methods.

For DNA modifications that cannot be converted to strand-breaks, there are existing methods that allow, in some cases, mapping of the modifications across genomes, such as single-molecule, real-time (SMRT) sequencing technology[13]. SMRT sequencing has been applied for direct mapping of phosphorothioate DNA modifications across bacterial genomes.[13] However, SMRT sequencing requires specific instrumentation as well as highly specialized software programming skills to optimize the sequencing signal for a specific modification, with many modifications not revealed by SMRT. Phosphorothioate modifications represent an example of a modification that can be converted to a strand break site-specifically,[13] with the single-strand breaks amenable to Nick-seq™ sequencing.

In summary, the nick translation sequencing methodology provides a universal method for mapping single-strand breaks across genomes, with significant advantages in cost, time, resolution and sensitivity over existing methods.

The commercial applications of the Nick-seq™ sequencing methodology are many. All commercial applications would derive from a basic kit containing α-thio-dNTPs, ddNTP such as ddCTP, buffers, and enzymes to allow blocking of existing nicks (if needed) and nick translation of nicks of interest. The PT-labeled DNA product of nick translation would then be subjected to deep-sequencing using any platform available to the user. For specialized applications that require processing of DNA features into strand-breaks, the kit would be accompanied by accessory kits containing specific enzymes and buffers, and/or detailed instructions for converting the feature into a nick-translatable strand break. For example, phosphorothioate modifications can be converted to single-strand breaks by treatment with iodine, with the results nicks readily mapped by Nick-seq™ sequencing.[13] As another example, an accessory kit with FAPY glycosylase (wide commercially available) would allow mapping of 8-oxoguanine and other purine DNA lesions across a genome by nick translation.

Examples of applications of the Nick-seq™ kit include:
m5C methylation—an accessory kit containing TET or TDG enzyme that specifically converts m5C to an abasic site along with the AP endonuclease that converts abasic sites to nick translation-amendable strand breaks.

Other DNA modifications—accessory kits or instructions for chemical or enzymatic conversion of specific DNA modifications into single-strand breaks.

DNA lesions—accessory kits containing specific enzymes that convert DNA damage products to single-strand breaks, as noted earlier for 8-oxoguanine.

DNA repair mechanisms—as noted earlier, no accessory enzymes would be needed in many cases and the single-strand gaps and nicks resulting from the repair process could be mapped directly using the Nick-seq™ methodology. Accessory kits or instructions for cleaning up repair-induced single-strand gaps or nicks are described below.

DNA single-strand breaks—in most cases, no accessory kit is needed. However, some types of DNA-damaging agents cause single-strand breaks that contain sugar residues that could block nick translation. Here an accessory kit could be provided containing enzymes that remove the sugar residues (widely commercially available), or instructions for using these enzymes to "clean up" the strand breaks.

DNA structures—as described earlier, many DNA secondary structures can be converted to single-strand breaks by chemicals such as hydroxyl radicals or ionizing radiation. These nicks can then be directly nick translated using the basic kit.

Chromatin structures—proteins binding to DNA in the nucleus of eukaryotic cells or in bacteria protect the DNA from nicking by many types of DNA-nicking enzymes, with the resulting nick sites in unprotected DNA providing a substrate for the Nick-seq™ kit. The genomic map of nick sites would reveal stretches of DNA lacking nicks, which represent the binding sites of proteins. Immunoprecipitation of specific proteins bound to DNA would reveal which proteins are associated with the nick-free "footprints" revealed by nick translation. However, the immunoprecipitation results would not provide the level of resolution needed to define the precise binding site, which is the power of the Nick-seq™ method.

Identifying an organism whose genome contains a specific modification—studies of DNA modifications in individual microbes in complex mixtures of microorganisms, such as the gut microbiome with 1000's of bacteria and viruses, are facilitated by the Nick-seq™ methodology. For example, a large portion of the bacteria in the human gut microbiome contain phosphorothioate modifications of their genomes. However, there is not technology available to identify the organisms actually containing the modification. The Nick-seq™ sequencing methodology allows labeling of single-strand breaks resulting from iodine treatment of the modified DNA, with subsequent sequences of the labeled DNA useful for defining the genus, species and strain of the bacterium by overlying the sequences on the organism's genome.

The kits are applicable to a wide variety of genomic studies in diverse areas of biology, biomedical research and biotechnology, including genetics, genomics, molecular and cell biology, microbiology, biotechnology, medicine, and clinical research, toxicology, pharmacology and other areas. Research and development in nearly every type of human disease involves genome-wide analyses of DNA damage and repair, modifications and chromatin structures and would benefit from the methodologies provided herein.

EXAMPLES

Example 1. Analysis of Standard Mixtures Containing Oligos of Varying Lengths and Abundances In the first example, five mixtures consisting of five RNA oligos between 25 and 80 nucleotides in length spiked at different abundances were created. Each mixture was then split into three technical replicates. All the samples were further spiked with a defined quantity of a 80-mer synthetic RNA oligonucleotide as an internal standard.

Figure 2:
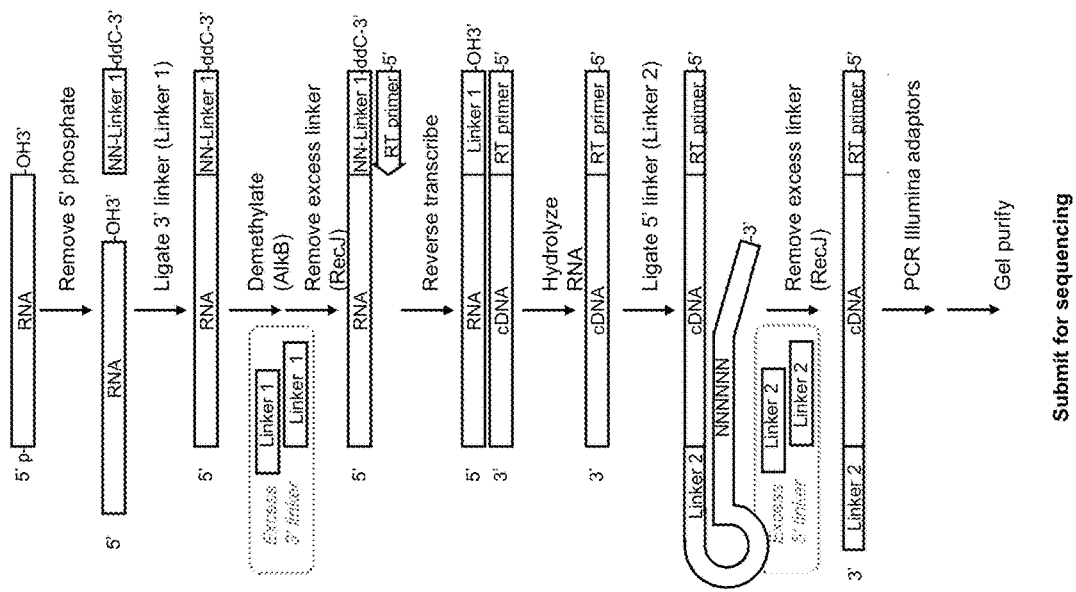
FIG. 2: A novel method for RNA (such as tRNA) sequencing that provides absolute quantification of RNA molecules in a single sample. The first illustrated step comprises removing the 5' phosphate from the RNA, for example using a phosphatase enzyme. The resultant RNA is then ligated to a linker (e.g., linker 1), for example using T4 RNA ligase I. Pre-ligation, the linker may be present in excess, e.g., 100-fold excess, compared to the RNA. Thereafter, a demethylation reaction, for example using AlkB enzyme, may be performed, optionally followed by a 5' deadenylase reaction, after which a RecJ digestion may also be performed. The latter reaction helps to remove excess unligated linker. Reverse transcription is then performed in the presence of RT primers and the RNA template is then degraded (e.g., by hydrolyzing the RNA), thereby leaving behind the cDNA which is then ligated to a 5' linker (linker 2), for example using T4 DNA ligase. Linker 2 may be present in excess compared to the cDNA, including on the order of about 50-fold excess. Excess unligated linker 2 is then also removed, for example using RecJ digestion. Thereafter, the cDNA ligated at its 5' and 3' ends with linker 1 and 2, respectively, may be amplified using for example PCR (using, for example, Illumina adaptors and/or barcodes), then optionally purified, and further optionally sequenced.

The RNA samples were then subjected to the series of reactions shown in FIG. 2 to prepare a library for RNA sequencing. The methodological details are presented here.

Step #1, Dephosphorylate the RNA

A mixture of tRNA (40 ng; ~2 pmol), 50-mer RNA internal standard, NEB T4 RNA ligase buffer (0.5 µL; New England Biolabs), shrimp alkaline phosphatase (1 µL, New England Biolabs) and water in 5 µL was incubated at 37° C. for 30 minutes and the reaction stopped by heat inactivation at 65° C. for 5 minutes. RNA denaturation was maintained by holding the samples on ice for the next step.

Step #2, Ligate Linker 1 to the RNA

Figure 3:
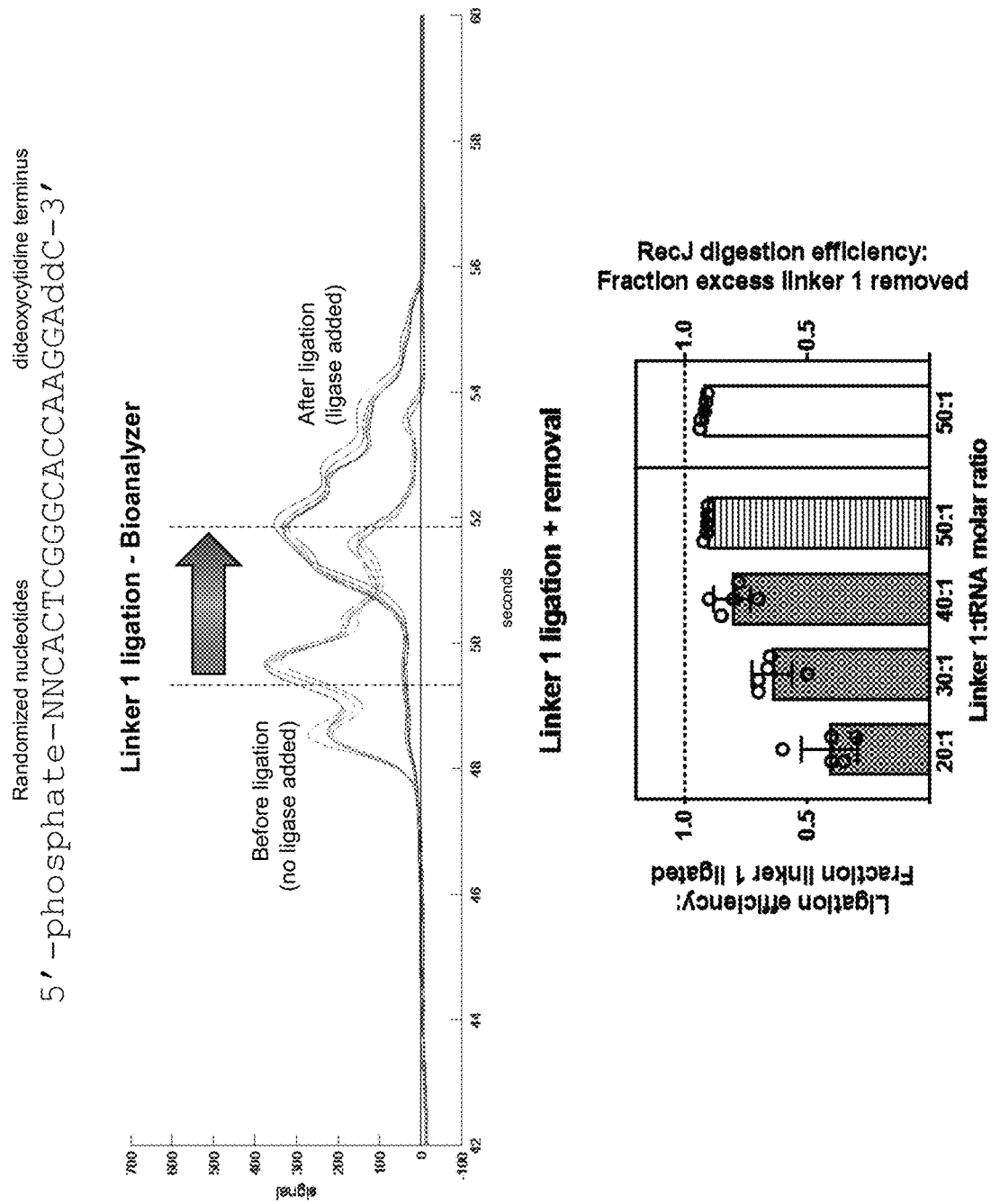
FIG. 3: Ligation of Linker 1 to tRNA in Step (b). Upper: Linker 1 structure and sequence. NN, randomized nucleotides; ddC, dideoxycytidine. In some embodiments, Linker 1 has the sequence of 5'-phosphate-NNCACTCGGGCAC-CAAGGA-ddC-3' (SEQ ID NO: 1), as shown. In some embodiments, Linker 1 has the sequence of 5'-phosphate-NN-CACTCGGGCACCAGGA-ddC-3' (SEQ ID NO: 2). Middle: A Bioanalyzer electropherogram showing an increase in the size of the tRNA starting material after Linker 1 ligation. The left stippled vertical line represents the size of the tRNA before ligation and the right stippled vertical line represents the size of the tRNA-Linker 1 ligation product. The difference between those lines represents the length of the linker. In some instances, the linker may be 20 nucleotides in length. Lower: Integration of Bioanalyzer traces reveals highly efficient (>91%) ligation of Linker 1 to tRNA when Linker 1 is present at a ratio of 50:1 relative to the RNA starting material. Removal of a 50-fold excess of Linker 1 using deadenylase and recJ is highly efficient as well (>92% of excess, unligated Linker 1 is shown to be removed).

To the 10 µL dephosphorylation mixture from Step #1 was added 10 µL of a master mix of 1 µL of Linker 1 (100 pmol/µL; sequence in FIG. 3; IDT) 3 µL ATP (10 mM; NEB), 2.5 µL of T4 RNA ligase buffer (NEB), 2 µL of T4 RNA ligase 1 (30 U/µL; NEB), and 15 µL of PEG8000 in 1.5 uL water (Sigma). The mixture was incubated at 16° C. overnight. Zymo Oligo Clean & Concentrator kit was used to clean up the completed ligation. The linker-ligated RNA was isolated in 20 µL of water and held on ice for the next step. Bioanalyzer quantitation of the original and linker-ligated tRNA revealed that the ligation was >91% efficient, as shown in FIG. 3.

Step #3, Reduce the Level of RNA Modifications

The 20 µL of linker-ligated tRNA from Step #2 was mixed with 50 µL of freshly-prepared, 2×-concentrated optimized AlkB buffer mixture (150 µM 2-ketoglutarate, 4 mM L-ascorbic acid, 150 µM $(NH_4)_2Fe(SO_4)_2$ $6H_2O$, 100 µg/mL BSA, 100 mM HEPES, pH8; slight purple color that turns brown over time), 2 µL of AlkB enzyme (ArrayStar), 1 µL RNase Inhibitor (NEB) and 27 µL of water. The reaction was incubated at ambient temperature for 2 h, followed by denature of AlkB by heating at 65° C. for 5 minutes AlkB protein was removed by extraction with 100 µL of phenol:chloroform:isoamyl alcohol 25:24:1, pH 5.2. The aqueous layer (~90 µL) was washed once with 100 µL of chloroform. The RNA in the aqueous layer (~75 µL) was purified using the Zymo kit noted earlier, with the RNA eluted into 16-20 µL of water.

Step #4, Remove Excess Linker 1

The purified RNA from Step #3 was first treated with deadenylase to remove the 5'-adenylpyrophosphoryl group remaining on Linker 1 as an intermediate from the ligase reaction. Removal of the 5'-adenylation is necessary for Rec J-mediated degradation of the Linker 1. The deadenylation reaction consisted of the 16-20 µL of linker-ligated RNA product from Step #3, 2 µL of NEB Buffer #2 and 2 µL of 5'-deadenylase (NEB). The reaction was allowed to proceed at 30° C. for 1 hour. Linker 1 in this mixture was then hydrolyzed by adding 2 µL of Rec J enzyme (30 U/µL; NEB), incubating at 37° C. for 30 minutes, adding another 2 µL of RecJ and incubating again at 37° C. 30 minutes. RNA was purified using a Dyex Kit (Qiagen) according to manufacturer's instructions, with the final eluted RNA reduced to 24 µL under vacuum.

Step #5, Reverse Transcription of the Linker-Ligated RNA

Figure 4:
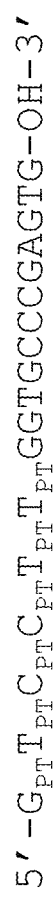
FIG. 4: An exemplary RT primer structure and sequence are provided. PT in subscript, phosphorothioate linkage. As shown, this RT primer has the sequence of (SEQ ID NO: 3)
5'-G$_{PT}$T$_{PT}$C$_{PT}$C$_{PT}$T$_{PT}$T$_{PT}$GGTGCCCGAGTG-OH-3'.

The purified linker-ligated RNA from Step #4 was next subjected to reverse transcription to create a cDNA copy. The key feature here is the use of an oligodeoxynucleotide primer (RT primer, reverse complementary to Linker 1) possessing 6 phosphorothioate linkages at the 5'-end (FIG. 4), which prevents degradation of the cDNA by Rec J in Step #8. The reverse transcription reaction starts by annealing RT primer to the linker-ligated RNA in a reaction consisting of 1 µL RT primer (2 pmol/µL), 1 µL of dNTPs (10 mM each), and the 24 µL of Dyex-purified RNA from Step #4. The mixture was heated at 80° C. for 2 minutes and cooled immediately on ice for 2 minutes. The reverse transcription reaction was initiated by adding 6 µL of 5× PrimeScript Buffer (Clonetech), 1 µL of RNase Inhibitor (NEB) and 1 µL of PrimeScript Reverse Transcriptase (Clonetech). This mixture was incubated at 50° C. for 2 hours. The enzyme was inactivated by heating at 70° C. for 15 minutes. Stopping point: this mixture can be stored at 4° C. indefinitely.

Step #6, Remove the RNA by Alkaline Hydrolysis and Purify cDNA

The cDNA was purified by first hydrolyzing the RNA by adding 1 µL of 5 M NaOH to 25 µL of the mixture from Step #5, with heating to 90-95° C. for 3 minutes. After cooling to ambient temperature, the pH was adjusted to 7 by adding 1 µL of 5 M HCl. The cDNA was then purified using the Zymo kit noted earlier, with the eluted cDNA evaporated to dryness under vacuum. Stopping point: the cDNA can be stored at −20° C. for at least one week.

Step #7, Ligate Linker 2 to the cDNA

The design of Linker 2 is shown in FIG. 5. Linker 2 is a uniquely-designed hairpin/splint oligodeoxynucleotide. The 6 randomized nucleotides ("N") allow hybridization to the 3'-ends of all possible cDNA sequences, while the hairpin structure ensures proximity of the 5'-end of the linker with the 3'-end of the cDNA. As a result, the efficiency of ligation with T4 DNA ligase is >96% (FIG. 5). The ligation reaction consists of 1 µL of Linker 2 (50 pmol/µL), 2 µL of T4 DNA ligase buffer (NEB), 1 µL ATP (10 mM), 5 µL cDNA from Step #6 (resuspended in water), 2 µL of T4 DNA ligase, and 9 µL of PEG 8000. The sample was mixed and incubated at 16° C. overnight. The ligation products were purified using the Zymo kit noted earlier and eluted with 16 µL of water.

Step #8, Remove Excess Linker 2

The remainder of Linker 2 was removed with by deadenylation and Rec J treatment as noted earlier, to reduce ligation artifacts during Step #9. The reaction starts with deadenylation 5'-adenylated Linker 2 (16 µL ligation mixture from Step #7, 2 µL of NEB Buffer 2, and 2 µL of 5'-deadenylase (add separately; no master mix). Following 1 hour incubation at 30° C., 2 µL of RecJ (30 U/µL) was added, the sample incubated for 30 minutes at 37° C., another 2 µL of RecJ was added with an additional 30 minutes incubation at 37° C. If Clonetech Polymerase is used in Step #9, then the sample (24 µL) can be proceed directly to the PCR reaction. If a Q5 PCR kit is used in Step #9, then change the buffer conditions by Dyex kit purification of the ligated DNA, with the eluted DNA evaporated to dryness and resuspended in 17 μL of water.

Step #9, PCR Attachment of Standard Illumina Primers

The final step involves attachment of standard Illumina PCR primers as shown in FIG. 2, according to the manufacturer's instructions. These primers introduce Illumina anchor sequences and sample-identifying barcodes to the prepared cDNA libraries. As shown in FIG. 6, Illumina PCR primer 1 contains the reverse complement of the 22 nt at the 5'-end of Linker 2, while Illumina PCR primer 2 contains the reverse complement to the 18 nt at 3'-end of Linker 1.

Figure 7:
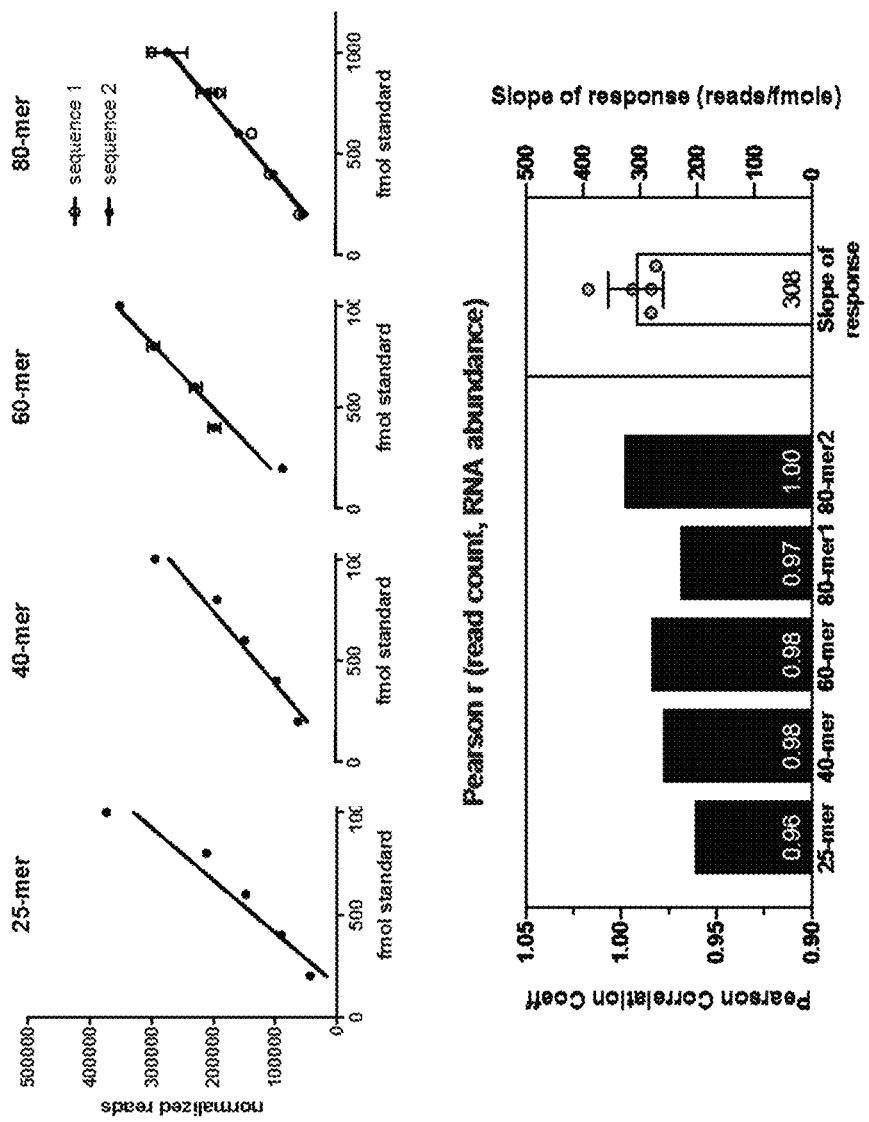
FIG. 7: Top: The RNA sequencing method of this disclosure reveals a strong linear relationship between the sequencing read count and the number of copies of spiked-in RNA internal standards that range in length from 25 to 80 nucleotides in length. Lower: Plot of Pearson Correlation Coefficient (read count, RNA abundance) for each RNA standard. Standard sizes are shown.

Following this series of reactions in Steps #1-#9, the sample was sequenced on the Illumina platform and the data mined using standard alignment workflow. The number of read counts for each RNA oligo standard and for the 80-mer internal standard were quantified. As shown in FIG. 7, the RNA sequencing method revealed a direct, linear correlation between the sequencing read count and the number of copies of each of the standards. The slope of the sequencing response (fmol of standard/normalized read count) was consistent between the five standards despite the wide variation in length from 25 to 80 nucleotides. This indicates that length does not significantly bias sequencing response.

Example 2. Analysis of Equimolar microRNA Standards

Figure 8:
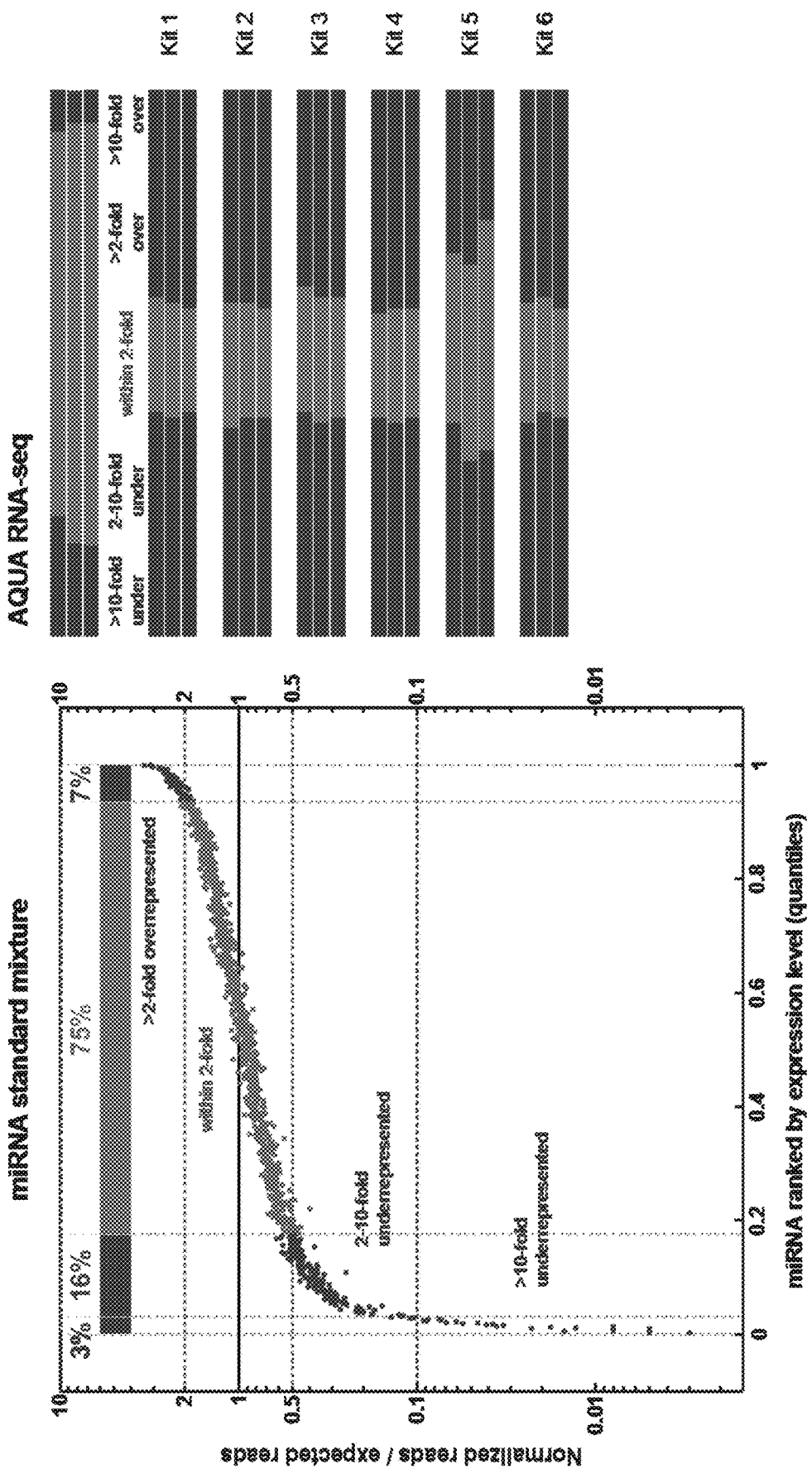
FIG. 8: Left: Among an equimolar mixture of over 900 microRNA standards, 75% were detected within two-fold of their expected abundance (i.e., between 0.5-2 on the Y axis). Right: Data obtained from an ABRF DSRG (The Association of Biomolecular Resource Facilities, DNA Sequencing Research Group) study comparing various commercially available small RNA library preparation kits. Data from AQUA-RNAseq outperforms kits tested. These methods show a far more varied output across kit types, with only about 20% of RNAs being detected within two-fold of their expected abundance. (The color version of this Figure, which is available upon request, illustrates the distribution more clearly.)

The second example involves using a commercially-available mixture of synthetically derived microRNA standards to determine the extent of sequence-dependent biases on quantification. The Miltenyi miRXplore universal reference contains 963 microRNA sequences that range from 16 to 29 nucleotides in length. The oligos are mixed together in an equimolar fashion. This sample represents a highly diverse pool of RNA sequences and the abundance of each sequence relative to any other should be 1. After applying the RNA sequencing method (Steps #1-#9), the ratio of the normalized read count to the expected read count was calculated for each standard. FIG. 8 shows the distribution of the ratios for all 963 microRNA sequences. 75% of the standards were detected to within two-fold of their expected abundance suggesting that sequence-dependent biases (especially from biases due to ligase preference) did significantly not factor into the library preparation process.

Figure 9:
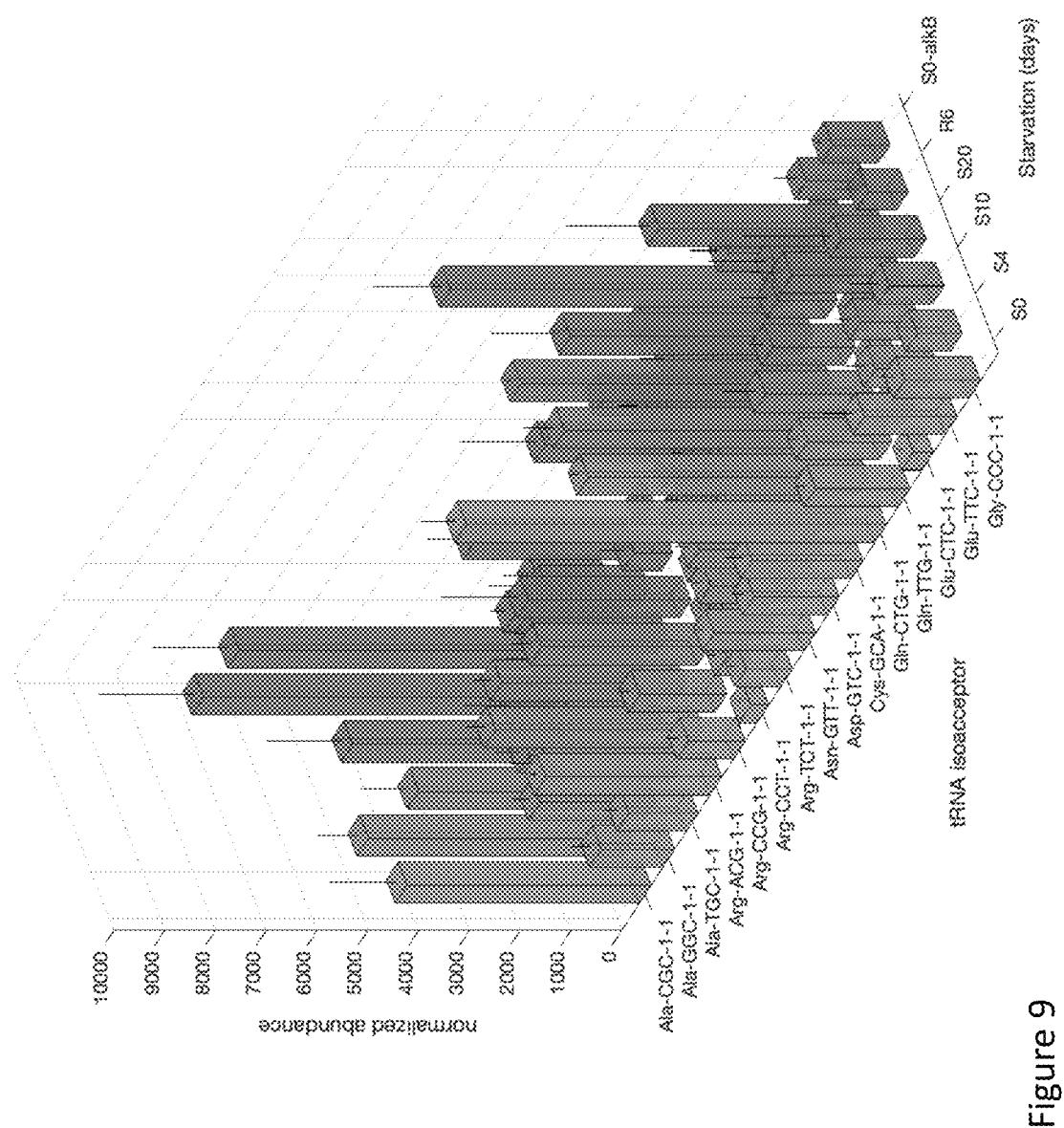
FIG. 9: The RNA sequencing method of this disclosure shows significant fluctuations in the number of copies of 15 different tRNA isoacceptors in *M. bovis* BCG subjected to starvation stress.

Example 3. Analysis of Starvation-Induced Changes in Small RNA Species in M. bovis BCG The third example of a reduction to practice for the RNA sequencing method of this disclosure involves analysis of the behavior of all small RNA species (<200 nt) in M. bovis BCG, a surrogate for the tuberculosis-causing M. tuberculosis, subjected to the stress of nutrient deprivation. Samples of small RNA species were isolated from BCG during growth in nutrient-rich medium (S0), on days 4, 10 and 20 after growth in nutrient-free phosphate-buffered saline (S4-S20), and on day 6 after returning the bacteria to nutrient-rich medium (resuscitation, R6). The RNA was processed for the RNA sequencing method in Steps #1-#9 described earlier and the resulting linker-ligated cDNA subjected to Illumina sequencing. As shown in FIG. 9, the behavior of 15 different tRNA isoacceptors (out of 47 total tRNAs) is observed to change dramatically during the starvation and resuscitation. For example, the number of copies of tRNA Lys-CTT-1-1 exceeds that of tRNA Phe-GAA-1-1 by a factor of ~3 during growth in nutrient-rich medium (S0). However, the Phe tRNA increases during early starvation (S0-S10), while there is a sharp drop in the number of copies of tRNA Lys-CTT-1-1 to nearly the same level as tRNA Phe-GAA-1-1 on day S10 (FIG. 9). This kind of direct comparison of RNA levels in the same sample would not be possible by any current RNA sequencing method.

REFERENCES

1. Gu C, Begley T J, Dedon P C. tRNA modifications regulate translation during cellular stress. FEBS Lett. 2014; 588(23):4287-96. PMCID: 4403629.
2. Phizicky E M, Hopper A K. tRNA biology charges to the front. Genes Dev. 2010; 24(17):1832-60. PMCID: 2932967.
3. Zhang Z, Lee J E, Riemondy K, Anderson E M, Yi R. High-efficiency RNA cloning enables accurate quantification of miRNA expression by deep sequencing. Genome Biol. 2013; 14(10):R109. PMCID: PMC3983620.
4. Hafner M, Renwick N, Brown M, Mihailovic A, Holoch D, Lin C, Pena J T, Nusbaum J D, Morozov P, Ludwig J, Ojo T, Luo S, Schroth G, Tuschl T. RNA-ligase-dependent biases in miRNA representation in deep-sequenced small RNA cDNA libraries. RNA. 2011; 17(9):1697-712. PMCID: PMC3162335.
5. Linsen S E, de Wit E, Janssens G, Heater S, Chapman L, Parkin R K, Fritz B, Wyman S K, de Bruijn E, Voest E E, Kuersten S, Tewari M, Cuppen E. Limitations and possibilities of small RNA digital gene expression profiling. Nat Methods. 2009; 6(7):474-6.
6. Pang Y L, Abo R, Levine S S, Dedon P C. Diverse cell stresses induce unique patterns of tRNA up- and down-regulation: tRNA-seq for quantifying changes in tRNA copy number. Nucleic Acids Res. 2014; 42(22):e170. PMCID: 4267671.
7. Cai W M, Chionh Y H, Hia F, Gu C, Kellner S, McBee M E, Ng C S, Pang Y L, Prestwich E G, Lim K S, Babu I R, Begley T J, Dedon P C. A Platform for Discovery and Quantification of Modified Ribonucleosides in RNA: Application to Stress-Induced Reprogramming of tRNA Modifications. Methods Enzymol. 2015; 560:29-71. PMCID: PMC4774897.
8. Zheng G, Qin Y, Clark W C, Dai Q, Yi C, He C, Lambowitz A M, Pan T. Efficient and quantitative high-throughput tRNA sequencing. Nature Methods. 2015; 12:835-7.
9. Tate C M, Nunez A N, Goldstein C A, Gomes I, Robertson J M, Kavlick M F, Budowle B. Evaluation of circular DNA substrates for whole genome amplification prior to forensic analysis. Forensic Sci Int Genet. 2012; 6(2):185-90.
10. Chiu T-P, Yang L, Zhou T, Main B J, Parker S C J, Nuzhdin S V, Tullius T D, Rohs R. GBshape: a genome browser database for DNA shape annotations. Nucleic Acids Research. 2014.
11. Li W, Hu J, Adebali O, Adar S, Yang Y, Chiou Y Y, Sancar A. Human genome-wide repair map of DNA damage caused by the cigarette smoke carcinogen benzo[a]pyrene. Proc Natl Acad Sci USA. 2017; 114(26):6752-7. PMCID: PMC5495276.
12. Zhou Z X, Zhang M J, Peng X, Takayama Y, Xu X Y, Huang L Z, Du L L. Mapping genomic hotspots of DNA damage by a single-strand-DNA-compatible and strand-specific ChIP-seq method. Genome Res. 2013; 23(4):705-15. PMCID: PMC3613587.

13. Cao B, Chen C, DeMott M S, Cheng Q, Clark T A, Xiong X, Zheng X, Butty V, Levine S S, Yuan G, Boitano M, Luong K, Song Y, Zhou X, Deng Z, Turner S W, Korlach J, You D, Wang L, Chen S, Dedon P C. Genomic mapping of phosphorothioates reveals partial modification of short consensus sequences. Nat Commun. 2014; 5:3951. PMCID: 4322921.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for analyzing modifications in naturally occurring nucleic acids comprising,
 (a) incubating a naturally occurring nucleic acid with a first polymerase and a ddNTP under conditions sufficient to fill in one or more single-stranded nicks in the nucleic acid,
 (b) treating the nucleic acid to convert a nucleic acid modification into a single-stranded nick, wherein the nucleic acid modification is a phosphorothioate modification, a methyl5C modification, or a DNA damage modification that is 8-oxoguanine, thereby generating a nicked nucleic acid,
 (c) incubating the nicked nucleic acid with a second polymerase and alpha-thio-dNTPs under conditions sufficient to generate a phosphorothioate-labeled nucleic acid fragment, and
 (d) mapping the phosphorothioate-labeled nucleic acid fragment onto a genomic map corresponding to a source of the naturally occurring nucleic acid to determine location of modifications in the naturally occurring nucleic acid,
 wherein the naturally occurring nucleic acid is DNA.

2. The method of claim 1, wherein the ddNTP is dideoxycytidine.

3. The method of claim 1, wherein the treating of step (b) is enzymatically, chemically and/or mechanically treating.

4. The method of claim 1, wherein the first polymerase and/or the second polymerase is DNA polymerase I.

5. The method of claim 1, wherein the nucleic acid modification is a phosphorothioate modification, wherein said nucleic acid modification is converted into a single-stranded nick using iodine.

6. The method of claim 1, wherein the nucleic acid modification is a methyl5C modification, wherein said nucleic acid modification is converted into a single-stranded nick using TET or TDG enzyme that converts a methyl5C to an abasic site and an AP endonuclease that converts abasic sites to single-stranded nicks capable of nick translation.

7. The method of claim 1, wherein the nucleic acid modification is a DNA damage modification that is 8-oxoguanine, wherein said nucleic acid modification is converted into a single-stranded nick using FAPY glycosylase.

8. The method of claim 1, wherein the phosphorothioate-labeled nucleic acid fragment is 100-500 nucleotides in length.

9. A method for detecting and mapping one or more modifications in a naturally occurring DNA sample comprising
(a) incubating a DNA sample with DNA polymerase I and dideoxycytidine under conditions sufficient to fill in and/or block existing single-stranded nicks in the naturally occurring DNA sample,
(b) treating the DNA sample to convert existing DNA modifications into single-stranded nicks, wherein said treating is enzymatically, chemically or mechanically treating, thereby generating nicked DNA, wherein the DNA modification is a phosphorothioate modification, a methyl5C modification, or a DNA damage modification that is 8-oxoguanine,
(c) incubating the nicked DNA with alpha-thio-dNTPs and DNA polymerase I under conditions sufficient to generate phosphorothioate-labeled DNA fragments through a process of nick translation/strand displacement, wherein said fragments are at least 100-500 nucleotides in length,
(d) incubating the DNA sample with nuclease P1 or an endo- or exo-nuclease that does not cleave phosphorothioate-labeled DNA fragments,
(e) isolating the phosphorothioate-labeled DNA fragments,
(f) amplifying and sequencing the phosphorothioate-labeled DNA fragments to generate sequencing reads, and
(g) mapping the sequencing reads onto a genomic map of the source of the naturally occurring DNA sample to determine location of the DNA modifications in the naturally occurring DNA sample.

10. The method of claim 9, wherein the DNA modification is a phosphorothioate modification, wherein said nucleic acid modification is converted into a single-stranded nick using iodine.

11. The method of claim 9, wherein the DNA modification is a methyl5C modification, wherein said nucleic acid modification is converted into a single-stranded nick using TET or TDG enzyme that converts a methyl5C to an abasic site and an AP endonuclease that converts abasic sites to single-stranded nicks capable of nick translation.

12. The method of claim 9, wherein the DNA modification is a DNA damage modification that is 8-oxoguanine, wherein said nucleic acid modification is converted into a single-stranded nick using FAPY glycosylase.

13. A method for detecting and mapping one or more nucleic acid lesions in a naturally occurring nucleic acid sample comprising
(a) incubating a nucleic acid sample with a polymerase and alpha-thio-dNTPs under conditions sufficient to generate a phosphorothioate-labeled nucleic acid fragment,
(b) removing unlabeled nucleic acids under conditions that specifically degrade said unlabeled nucleic acids and do not degrade the phosphorothioate-labeled nucleic acid fragment, and
(c) mapping the phosphorothioate-labeled nucleic acid fragment onto a genomic map corresponding to a source of the naturally occurring nucleic acid sample to determine location of the one or more nucleic acid lesions.

14. The method of claim 13, wherein the polymerase is DNA polymerase I.

15. A kit comprising alpha-thio-dNTPs, ddNTP, wherein the ddNTP is or comprises dideoxycytidine, a polymerase, and a buffer(s), iodine, FAPY glycosylase, TET or TDG enzyme capable of converting a methyl5C to an abasic site, an enzyme capable of converting a DNA damage lesion to a single-stranded nick, an enzyme capable of removing a sugar residue from a nucleic acid, hydroxyl radicals, or a chemical capable of generating hydroxyl radicals, and instructions directing use according to the method of claim 1.

16. A method for measuring RNA in a sample comprising
(a) dephosphorylating RNA in a sample, thereby generating dephosphorylated RNA,
(b) ligating, to the dephosphorylated RNA, a ddNTP-ended oligodeoxynucleotide linker having two or more randomized nucleotides at its 5'-end (Linker 1), thereby generating a linker-ligated RNA,
(c) optionally treating the linker-ligated RNA conjugate with an AlkB enzyme capable of reducing level of RNA modification,
(d) removing excess Linker 1 by treating with dead-enylase to remove a ligase-mediated intermediate and then degrading Linker 1 with the 2'-deoxyribonuclease Rec J,
(e) reverse transcribing the linker-ligated RNA into cDNA using a primer complementary to (e) Linker 1 and reverse transcriptase,
(f) degrading residual RNA,
(g) ligating a hairpin/splint oligodeoxynucleotide linker comprising a double-stranded stem region, a single-stranded loop region, a random nucleotide sequence region capable of hybridizing to the cDNA, and a single-stranded 3' end (Linker 2) to the cDNA,
(h) removing excess Linker 2 by treating with dead-enylase to remove a ligase-mediated intermediate and then degrading Linker 2 with the 2'-deoxyribonuclease Rec J, and
(i) amplifying the linker-ligated cDNA using primers that comprise reverse complements of sequences in Linkers 1 and 2 (Primer 1 and Primer 2).

17. A kit comprising DNA oligonucleotides, a ddNTP-ended oligodeoxynucleotide linker having two or more randomized nucleotides at its 5'-end (Linker 1), a hairpin/splint oligodeoxynucleotide linker comprising a double-stranded stem region, a single-stranded loop region, a random nucleotide sequence region capable of hybridizing to a cDNA, and a single-stranded 3' end (Linker 2), a reverse transcription (RT) primer, and primers that comprise reverse complements of sequences in Linkers 1 and 2 (Primer 1 and Primer 2).

18. The method of claim 1, further comprising removing unlabeled nucleic acids under conditions that specifically degrade said unlabeled nucleic acids and do not degrade the phosphorothioate-labeled nucleic acid fragment prior to step (d).

19. The method of claim 1, further comprising isolating or purifying the phosphorothioate-labeled nucleic acid fragment prior to step (d).

20. The method of claim 1, further comprising amplifying and/or sequencing the phosphorothioate-labeled nucleic acid fragment prior to step (d).

21. The method of claim 9, wherein step (e) is conducted by ethanol precipitation or column chromatography.

22. The method of claim 16, wherein:
   (i) in step (a) dephosphorylating RNA in a sample comprises using alkaline phosphatase,
   (ii) in step (b) the ddNTP-ended oligodeoxynucleotide linker is dideoxycytidine-ended oligodeoxynucleotide linker,
   (iii) in step (c) the AlkB enzyme is a mutant AlkB enzyme,
   (iv) in step (f) degrading residual RNA includes degrading RNA that is not linker-ligated,
   (v) in step (f) degrading residual RNA includes degrading RNA using alkaline hydrolysis, and/or
   (vi) in step (g) ligating the hairpin/splint oligodeoxynucleotide linker (Linker 2) to the cDNA comprises using T4 DNA ligase.

\* \* \* \* \*

SEQUENCE LISTING

<160> NUMBER OF SEQ ID NOS: 22

<210> SEQ ID NO 1
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (20)..(20)
<223> OTHER INFORMATION: dideoxycytidine

<400> SEQUENCE: 1
nncactcggg caccaaggac                                               20

<210> SEQ ID NO 2
<211> LENGTH: 19
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (19)..(19)
<223> OTHER INFORMATION: dideoxycytidine

<400> SEQUENCE: 2
nncactcggg caccaggac                                                19

<210> SEQ ID NO 3
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
<223> OTHER INFORMATION: phosphothioate linkage between the indicated
      residues
<220> FEATURE:
<221> NAME/KEY: misc_feature
<222> LOCATION: (2)..(3)
<223> OTHER INFORMATION: phosphothioate linkage between the indicated
      residues
<220> FEATURE:
<221> NAME/KEY: misc_feature
<222> LOCATION: (3)..(4)
<223> OTHER INFORMATION: phosphothioate linkage between the indicated
      residues
<220> FEATURE:
<221> NAME/KEY: misc_feature
<222> LOCATION: (4)..(5)
<223> OTHER INFORMATION: phosphothioate linkage between the indicated
      residues
<220> FEATURE:
<221> NAME/KEY: misc_feature
<222> LOCATION: (5)..(6)
<223> OTHER INFORMATION: phosphothioate linkage between the indicated
      residues
<220> FEATURE:
<221> NAME/KEY: misc_feature
<222> LOCATION: (6)..(7)
<223> OTHER INFORMATION: phosphothioate linkage between the indicated
      residues

<400> SEQUENCE: 3
gtccttggtg cccgagtg                                                          18

<210> SEQ ID NO 4
<211> LENGTH: 40
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (23)..(28)
<223> OTHER INFORMATION: n is a, c, g, or t
<220> FEATURE:
<221> NAME/KEY: misc_feature
<222> LOCATION: (40)..(40)
<223> OTHER INFORMATION: modified by propyl spacer

<400> SEQUENCE: 4
tgaagagcct agtcgctgtt cannnnnnct gcccatagag                                  40

<210> SEQ ID NO 5
<211> LENGTH: 41
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (23)..(28)
<223> OTHER INFORMATION: n is a, c, g, or t
<220> FEATURE:
<221> NAME/KEY: misc_feature
<222> LOCATION: (41)..(41)
<223> OTHER INFORMATION: modified by propyl spacer

<400> SEQUENCE: 5
tgaagagcct agtcgctgtt cannnnnnct gcccatagag c                                41

<210> SEQ ID NO 6
<211> LENGTH: 90
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (30)..(35)
<223> OTHER INFORMATION: n is a, c, g, or t; barcode sequence

<400> SEQUENCE: 6
aatgatacgg cgaccaccga gatctacacn nnnnnacact ctttccctac acgacgctct            60
tccgatcttg aacagcgact aggctcttca                                             90

<210> SEQ ID NO 7
<211> LENGTH: 85
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (25)..(30)
<223> OTHER INFORMATION: n is a, c, g, or t; barcode sequence

<400> SEQUENCE: 7
caagcagaag acggcatacg agatnnnnnn cggtctcggc attcctgctg aaccgctctt            60

```
ccgatctgtc cttggtgccc gagtg                                            85

<210> SEQ ID NO 8
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 8
tgaccccggt ctacacattc gggagggcat agcatcaata gatgtgctgc ccctcagtcc      60
gtt                                                                   63

<210> SEQ ID NO 9
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 9
aacggactga ggggcagcac atctattgat gctatgccct cccgaatgug tagaccgggg      60
tca                                                                   63

<210> SEQ ID NO 10
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 10
acattcggga gggcatagca tcaatagatg tgctgcccct cagtccgtt                  49

<210> SEQ ID NO 11
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 11
aacggactga ggggcagcac atctattgat gctatgccct cccgaatgu                  49

<210> SEQ ID NO 12
<211> LENGTH: 63
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (49)..(49)
<223> OTHER INFORMATION: n is an AP site

<400> SEQUENCE: 12
aacggactga ggggcagcac atctattgat gctatgccct cccgaatgng tagaccgggg      60
tca                                                                   63

<210> SEQ ID NO 13
<211> LENGTH: 49
<212> TYPE: DNA
<213> ORGANISM: Artificial Sequence
<220> FEATURE:
<223> OTHER INFORMATION: Synthetic Polynucleotide
```

```
<220> FEATURE:
<221> NAME/KEY: misc_feature
<222> LOCATION: (49)..(49)
<223> OTHER INFORMATION: n is an AP site

<400> SEQUENCE: 13
aacggactga ggggcagcac atctattgat gctatgccct cccgaatgn            49

<210> SEQ ID NO 14
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 14
tgaccccggt ctaccattc gggagggcat agcatcaata gatgtgctgc ccctcagtcc    60
gtt                                                                 63

<210> SEQ ID NO 15
<211> LENGTH: 63
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (49)..(49)
<223> OTHER INFORMATION: n is inosine

<400> SEQUENCE: 15
aacggactga ggggcagcac atctattgat gctatgccct cccgaatgng tagaccgggg   60
tca                                                                 63

<210> SEQ ID NO 16
<211> LENGTH: 49
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is a or c

<400> SEQUENCE: 16
ncattcggga gggcatagca tcaatagatg tgctgcccct cagtccgtt             49

<210> SEQ ID NO 17
<211> LENGTH: 49
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (49)..(49)
<223> OTHER INFORMATION: n is inosine

<400> SEQUENCE: 17
aacggactga ggggcagcac atctattgat gctatgccct cccgaatgn             49

<210> SEQ ID NO 18
<211> LENGTH: 63
<212> TYPE: DNA
<213> ORGANISM: Artificial Sequence
<220> FEATURE:
```

```
<223> OTHER INFORMATION: Synthetic Polynucleotide

<400> SEQUENCE: 18 tgacccggt ctactcattc gggagggcat agcatcaata gatgtgctgc ccctcagtcc    60
gtt                                                                63

<210> SEQ ID NO 19
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 19
aacggactga ggggcagcac atctattgat gctatgccct cccgaatgag tagaccgggg    60
tca                                                                63

<210> SEQ ID NO 20
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 20
tcattcggga gggcatagca tcaatagatg tgctgccct cagtccgtt                 49

<210> SEQ ID NO 21
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 21
aacggactga ggggcagcac atctattgat gctatgccct cccgaatga               49

<210> SEQ ID NO 22
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 22
ttcggcaaac ggcattccgt ctacccaaca cgaagc                             36
```